US006710036B2

(12) United States Patent
Kurtzman et al.

(10) Patent No.: US 6,710,036 B2
(45) Date of Patent: *Mar. 23, 2004

(54) INDUCTION OF IMMUNE RESPONSE TO ANTIGENS EXPRESSED BY RECOMBINANT ADENO-ASSOCIATED VIRUS

(75) Inventors: Gary J. Kurtzman, Menlo Park, CA (US); Edgar G. Engelman, Atherton, CA (US); Greg M. Podsakoff, Fullerton, CA (US); Dirk G. Brockstedt, Palo Alto, CA (US)

(73) Assignees: Avigen, Inc., Alameda, CA (US); Board of Trustees, Leland Stanford Jr. University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/858,728

(22) Filed: May 16, 2001

(65) Prior Publication Data

US 2002/0102243 A1 Aug. 1, 2002

Related U.S. Application Data

(63) Continuation of application No. 09/121,162, filed on Jul. 23, 1998, now Pat. No. 6,242,426.
(60) Provisional application No. 60/053,733, filed on Jul. 25, 1997.

(51) Int. Cl.[7] .................. A61K 48/00; C12N 15/63; C12N 15/85
(52) U.S. Cl. .............. 514/44; 435/320.1; 435/325; 435/455; 424/93.1; 424/93.2
(58) Field of Search .................. 435/320.1, 325, 435/455; 424/93.1, 93.2; 514/44

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,708,871 A | 11/1987 | Geysen | |
| 4,946,778 A | 8/1990 | Ladner et al. | |
| 4,965,188 A | 10/1990 | Mullis et al. | |
| 5,139,941 A | 8/1992 | Muzyezka et al. | |
| 5,173,414 A | 12/1992 | Lebkowski et al. | |
| 6,242,426 B1 * | 6/2001 | Kurtzman et al. | 514/44 |

FOREIGN PATENT DOCUMENTS

| | | |
|---|---|---|
| WO | WO 90/13678 | 11/1990 |
| WO | WO 92/01070 | 1/1992 |
| WO | WO 92/08981 | 5/1992 |
| WO | WO 93/03367 | 2/1993 |
| WO | WO 93/03769 | 3/1993 |

OTHER PUBLICATIONS

Restifo et.al.; Molecular Mechanisms Used by Tumors toEscape Immune Recognition: Immunogenetherapy and the Cell . . . Complex, 1993, Journal of Immunotherapy 14: 182–190.*

Ross et.al.; Gene Therapy in the United States: A Five–Year Status Report, 1996, Human Gene Therapy 7: 1781–1790.*
Yasutomi et.al.; A Vaccine–Elicited, Single viral Epitope–Specific Cytotoxic T . . . Simian Immunodeficiency Virus Challenge, 1995, Journal of Virology: 2279–2284.*
Monteil et.al.; Genetic Immunization of seronegative one–day–old piglets against pseudorabies . . . in piglets from immune dams, 1996, Elsevier:444–452.*
ERtl et.al.; Genetic Immunization, 1996, Viral Immunology, vol. 9: 1–9/.*
Khleif, et.al., "A Phase I Vaccine Trial with Peptides Relecting ras Oncogene Mutations of Solid Tumors," Journal of Immunotherapy, vol. 22, No. 2 (Mar. 1999) 155–165.
Abbas et al., Nature, vol. 383, 787–793, 1996.
Ajello et al., "Adenovirus 5 DNA Sequences Present and RNA Sequence Transcribed in Transformed Human Embryo Kidney Cells (HEK–Ad–5 or 293)" Virol., 94:460–469 (1979).
Akidis et al., "Epitope–specific T Cell Tolerance to Phospholipase A, in Bee Venom Immunotherapy and Recovery bu IL–2 and IL–15 in Vitro", J. Clinic Inverstment, 18, 1676–1683, 1996.
Anderson, "Human Gene Therapy," Nature 392:25–30 (1998).
Anderson and Young, "Quantitative Filter Hybridization, in Nucleic Acid Hybridization", pp. 73–111, 1985.
Attays et al., "Ham–2 corrects the antigen–processing defect in RMA–S cells," Nature 355–647–649, 1992.
Barr et al., "Efficient Catheter–mediated gene transfer into the heart using replication–defective adenovirus," Gene Therapy, 1:51–58, 1994.
Bauer et al., "Modulation of the Allergic Immune Response in BALB/c mice by subcutaneous injection of high doses of the dominant T cell epitope from the major birch pollen allergen Bet v.1," Clin. Exp. Immunol., 107:536–541., 1997.
Berkner, "Development of Adenovirus Vectors for the Expression of Heterologous Genes," BioTechn., 6: 616–629, 1988.
Berns, "Parvoviridae and Their Replication" in Fundamental Virology, 2nd Edition, Fields and Knipe (eds.), pp. 817–837, Raven Press, New York, 1991.
Berns and Bohenzky, "Adeno–Associated Viruses: An Update, "Adv. Virus Res., 32: 243–306, 1987.
Bett et al., "Packaging Capacity and Stability of Human Adenovirus Type 5 Vectors," J. Virol., 67–5911–5921, 1993.
Boshart, et al., "A Very Strong Enhancer is Located Upstream of an Immediate Early Gene of Human Cytomegalovirus," Cell 41:521–530, 1985.

(List continued on next page.)

Primary Examiner—Anne M. Wehbé
(74) Attorney, Agent, or Firm—Stoel Rives LLP

(57) ABSTRACT

The present invention relates generally to immunization methods using recombinant viral vectors. In particular, the invention relates to methods and compositions for immunizing a subject with a nucleic acid molecule encoding an antigen of interest, wherein the nucleic acid molecule is delivered to the subject via a recombinant AAV virion.

18 Claims, 4 Drawing Sheets

OTHER PUBLICATIONS

Figure 1:
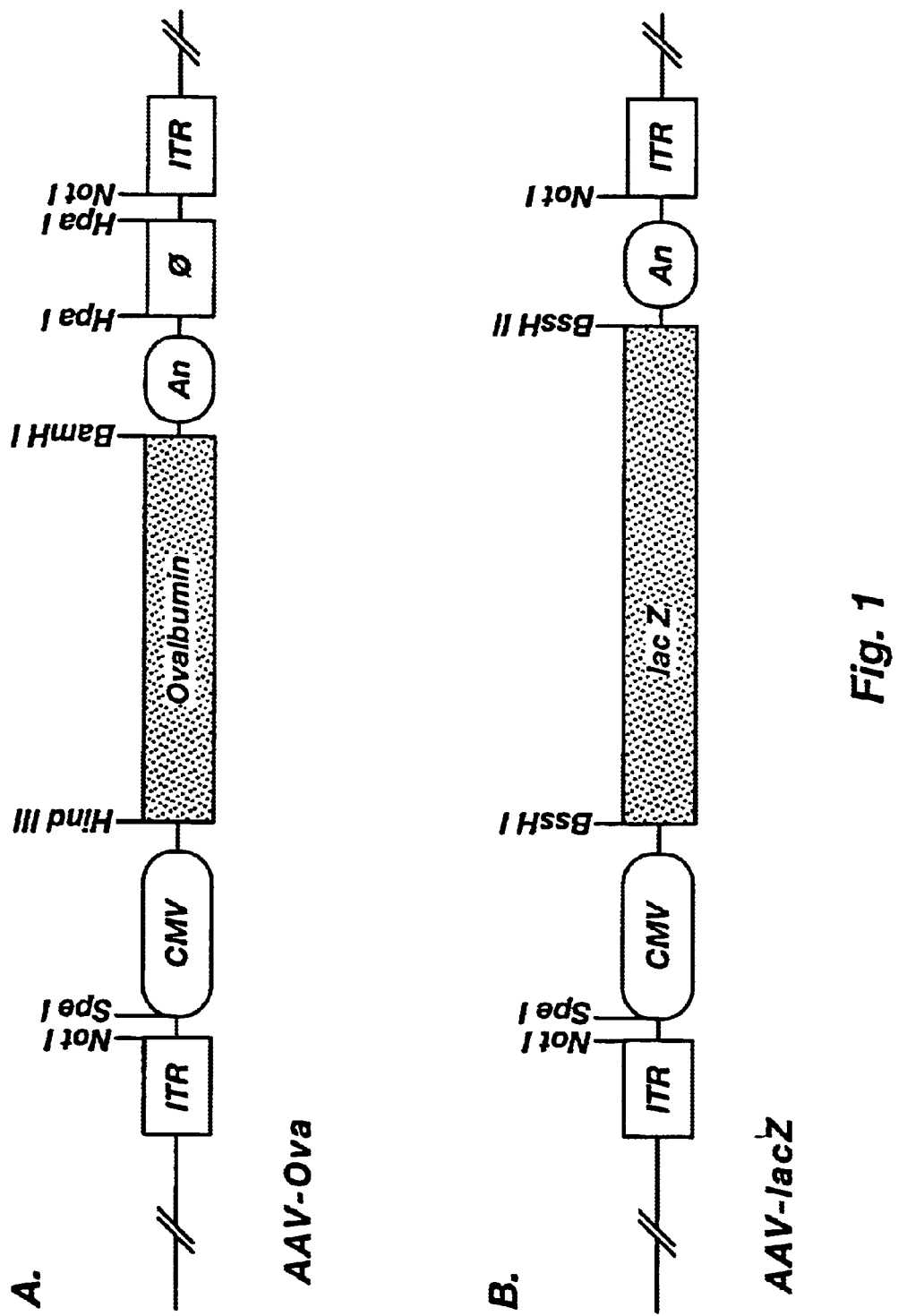

Butler et al., "Herpes Simplex Virus Types 1 and 2 Completely Help Adenovirus–Associated Virus Replication," J. Virol. 40, 241–47, 1981.

Byrnes et al, "Immunological Instability of Persistent Adenovirus Vectors in the Brain: Peripheral Exposure to Vector Leads to Renewed Imflammation Reduced Gene Expression, and Demyelination," J. Neuroscience 16: 3045–3055 (1996).

Cao et al., "Vaccination with a multi–epitopic recombinant allergen induces specific immune deviation via T–cell energy," Immunol, 90: 46–51, 1997.

Capecchi, "High Efficiency Transformation by Direct Microinjection of DNA into Cultured Mammalian Cells," Cell 22:479–488, 1980.

Carter, "Adeno–associated virus vectors," Current Opinion Biol., 3, 533–39, 1992.

Carter, "Adeno–Associated Virus Helper Functions," in CRC Handbook of Parvoviruses, Vol1 (P. Tijssen, ed.,) 533–39, 1990.

Chamberlin et al., "New RNA Polymerase from *Escherichia coli* infected with Bacteriophage T7," Nature 228:227, 1970.

Chao, et al., "Sustained Expression of Human Factor VIII in Mice Using a Parvovirus–Based Vecotr," Blood, vol. 95 No. 5, Mar. 1, 2000 1594–98.

Chu and Sharp,"SV40 DNA transfection of cells in suspension analysis of the efficiency of transcription and translation of T–antigen," Gene 13:197–202, 1981.

Cole et al., "The EBV–Hybridoma Technique and its Application to Human Lung Cancer," in Monoclonal Antibodies and Cancer Therapy, Alan R,. Liss, 77–96, 1985.

Cole et al., "Generation of Human Monoclonal Antibodies Reactive with Cellular Antigens," Proc., Natl. Acad. Sci., USA, 80, 2026–30, 1983.

Colosi et al., Blood 86 No. Suppl. 1, 627a, 1995.

Condon, DNA–based immunization by in vitro transfection of dendritic cells, Nature Med., 2, 1122–28, 1996.

Conrad et al., "Safety of Single–does Administration of an Adeno–associated Virus (AAV)–CFTR Vector in the Primate Lung." Gene Therapy., 3: 658–668 (1996).

Davis et al., Basic Methods in Molecular Biology, Elsevier, 1986.

Dijkema et al, Cloning and Expression of the Chromosomal Immune Interferon Gene of the rat, Embo J. 4, 761767, 1985.

Doe et al., Induction of HIV1 envelope (gp 120)–specific cytotoxic T lymphocyte responses in mice by recombinant CHO cell–derived gp120 is enhanced by enzymatic removal of N–linked glycans, Eur. J. Immunol., 24:2369–2376, 1994.

Edge et al., "Total Synthesis of a Human Leukocyte Interferon Gene," Nature 292:756–61, 1981.

Erickson et al., Hepatitis C. Virus–Specific, CTL, Responses in the Liver of Chimpanzees with Acute and Chronic Hepatitis C, J. Immunol., 151:4189–4199 (1993).

Erlich (ed.), PCR Technology, Stockton Press (1989) (Title and Copyright Pages only).

Falo Jr. et al., "Targeting antigen into the Phagocytic pathway in vivo induces protective tumour immunity," Nature Med., 1, 649–53, 1995.

Felgner et al., Lipofection: A highly efficient, lipid–mediated DNA–transfection procedure, Proc. Natl. Acad. Sci. USA 84:7413–17, 1987.

Fisher et al., "Recombinant adeno–associated virus for muscle directed gene therapy," Nature Med., 3:306–312, 1997.

Flotte et al., "Stable in vitro expression fo the cystic fibrosis transmembrance conductance regulator with an adeno–associated virus vector," Proc. Natl. Acad. Sci. USA, 90:10613–16017, 1993.

Geysen et al., "A Priori Delineation of a Peptide which Mimics a Discontinuous Antigenic Determinant," Mol. Immunol., 23, 709–15, 1986.

Geysen, et al., "Use of Peptide synthesis to probe Viral Antigens for Epitopes to a Resolution of a Single Amino Acid," Proc. Natl. Acad. Sci. USA 81:3998–4002, 1984.

Glover et al., (ed.,) DNA Cloning: A Practical Approach, vols. I & II, 2nd ed., Oxford, New York, IRL Press (1995) (Title and Copyright Pages Only).

Golding, et al. Am. J. Topr. Med. Hyg. vol. 50(4) 33–40.

Gorman et al., "The Rous srcoma virus long terminal repeat is a strong promoter when introduced into a variety of eukaryotic cells by DNA–medicated transfection," Proc. Natl. Acad. Sci. USA, 79, 6777–81, 1982.

Graham et al., "Characteristics of a Human Cell Line Transformed by DNA from Human Adenovirus Type 5," J. Gen. Virol., 36, 59–72.

Graham et al., "A new Technique for the Assay of Infectivity of Human Adenovirus Type 5," J. Gen. Virol, 52: 456–467, 1973.

Greenburg et al., Endocrine Soc., Jun. 9–11: Abstract 1206 (1993).

Haj–Ahmad and Graham,"Development of a Helper–Independent Human Adenovirus Vector and Its Use in the Transfer of the Herpes Simplex Virus Thymidine Kinase Gene," J. Virol. 57: 267–74, 1986.

Harlow and Lane, Antibodies: A Laboratory Manual, Cold Spring Harbor Laboratory Press, Cold Spring Harbor, NY 1988.

Harris et al., "Molecular Basis for Heterogeneity of the Humans p53 Protein," Mol Cell Biol., 6, 4650–56, 1986.

Hergoz, Roland W., "Stable Gene Transfer and Expression of Human Blood Coagulation Factor IX after intramuscular Injection of Recombinant Adeno–Associated Virus," Proc. Natl. Acad. Sci. USA, vol. 94, 5804–09, May , 1997.

Hoyne et al., "Inhibition of T–cell Responses by Feeding Peptides Containing Major and Cryptic Epitopes; Studies with the der p1 allergen," Immunol., 83, 190–95, 1994.

Huber et al., "Retroviral–mediated gene therapy for the Treatment of *Hepatocellular carcinoma*: An innovative approach for cancer therapy," Proc. Natl. Acad. Sci. USA 88:8039–43, 1991.

Huse et al., "Generation of a Large Combinatorial Library of the Immunoglobulin Repertoire in Phage Lambda," Science 246, 1275–81, 1989.

Janik et al., "Locations of Adenovirus Genes required for the Replication of Adenovirus–associated Virus," Proc. Natl. Acad. Sci. USA 78: 1925–1929, 1981.

Jay et al., "Chemical Synthesis of a Biologically Active Gene for Human Immune Interferon–y," J. Biol. Chem., 259, 6311–17, 1984.

Jooss et al., "Transduction of Dendritic Cells by DNA Viral Vectors Directs the Immune Response to Transgene Products in Muscle Fibers," J. Virol. 72 (5):4212–4223 (1998).

Kass–Eisler et al., "The impact of developmental stage, route of administration and the immune system on adenovirus–infected hepatocytes in vivo," Gene Therapy, 1: 395–402 (1994).

Karttunen et al., Detection of rare antigen–presenting cells by the lacZ T–cell activation assay suggests an expression cloning strategy for T–cell entigens, Proc. Natl. Acad. Sci. USA, 89, 6020–24, 1992.

Kaplitt et al., "Viral Vectors for Gene Delivery and Expression in the CNS," Methods: A Companion to Methods in Enzymology 10: 343–350 (1996).

Kessler et al., Gene delivery to skeletal muscle results in sustained expression and systemic delivery of a therapeutic protein, Proc. Natl. Acad. Sci. UAS 24, vol. 93, 14082–87, 1996.

Kim et al., "Use of the Human Elongation Factor 1a promoter as a versatile and efficient expression system.", Gene 91, 217–223, 1990.

Kim et al., "Quantitative Analysis of T Cell Activation," J. Immunol., 156: 2737–42, 1996.

Klein et al., "High–velocity microprojective for deliverying nucleic acids into living cells," Nature 327: 70–73, 1987.

Kohler and Milstein, "Continuous cultures of fused cells secreting antibody of predefined specificity." Nature, 256, 495–97, 1975.

Kotin, "Prospects for the Use of Adeno–Associated Virus as a Vector for Human Gene Therapy." Human Gene Ther. 5, 793–801, 1994.

Kozbor et al., "The production of monoclonal antibodies from human lymphocytes," Immunol. Today 4:72–79, 1983.

Lang, In Principles of Animal Virology, Jokik (ed.) 255–57, Appleton–Centruy–Crofts, New York, 1980.

Lebowski et al., Adeno–Associated Virus: a Vector System for Efficient Introduction and Integration of DNA into a Variety of Mammalian Cell Types, Mol. Cell. Biol., 8, 3988–96, 1988.

Liu, et al., "Recombinant Adeno–Associated Virus Expressing Human Papillomavirus Type 16 E7 Peptide DNA Fused with Heat Shock Protein DNA as a Potential Vaccine for Cervical Cancer," J. Virol. Mar., 2000, 2888–2894.

Maniatis et al., ":Regulation of Inducible and Tissue Specific Gene Expression," Science, 236, 1237–44, 1987.

Manning, et al., "Genetic Immunization with Adeno–Associated Virus Vectors Expressing Herpes Simplex Virus Type 2 Glycoproteins B and D," J. Virol. Oct., 1997, 7960–62.

Mannino et al., "Liposome Mediated Gene Transfer," BioTech., 6, 682–290, 1988.

Marshall et al., Science, vol. 269, 1050–1055 (1995).

Matusik et al., "Regulation of Prostatic Genes; role of androgens and zinc in gene expression," Biochem and Cell Biol., 64, 601–07, 1986.

McCarty et al., "Sequences Required for Coordinate Induction of Adeno–Associate Virus p19 and p 40 Promoters by Rep Protein," J. Virol., 65, 2936–45, 1991.

McKechnie et al., "Cross–reactive antigens in the pathogenesis of onchocerciasis," Ann Trop. Med. Parasitol, 876, 649–652, 1993.

McPherson et al., "Human Cytomegalovirus Completely Helps Adeno–Associated Virus Replication," Virol, 147, 217–22, 1985.

Mittereder, et al., "Evaluation of the Efficacy and Safety of In Vitro, Adenovirus–Mediated Transfer of the Human Cystic Fibrosis Transmembrance Conductance Regulator cDNA," Human Gene Therapy, 5, 717–29, 1994.

Mizuhima and Nagata, "pEF–BOS, a powerful mammalian expression vector," Nuc. Acids. Res., 18, 5322, 1990.

Mizuno et al., "Adeno–associated Virus Vector Containing the Herpes Simplex Virus Thymidine Kinase Gene Causes Complete Regression of Intracerebrally Implanted Human Gliomas in Mice, in Conjuction with Ganciclovir Administration," Jpn. J. Cancer Res., 89: 76–80 (1998).

Monaco, "A Molecular Model of MHC –restricted antigen processing," Immunol. Today 13, 173–78, 1992.

Muzyezka, "Use of Adeno–Associated Virus as a General Tradsduction Vector for Mammalian Cells," Curr. Top. Microbiol. Immunol., 158, 97–129, 1992.

Nambair et al., "Total Synthesis and Cloning of a Gene Coding for the Ribonuclease S. Protein," Science 223, 1299–1301, 1984.

Orkin, et al., "Report and Recommendations . . . " (1995).

Remington's Pharmaceutical Sciences 18th ed., Easton Pa: Mack Pub. Co., 1990.

Rich et al., "Development and Analysis of Recombinant Adenoviruses for Gene Therapy of Cystic Fibrosis," Human Gene Therapy, 4, 461–76, 1993.

Rock, A new foreign policy: MHC molecules monitor the outside world, Immunol, Today 17, 131–37, 1995.

Rodriguez, et al., "DNA Immunization with Minigenes: Low Frequency of Memory Cytotoxic T Lymphocytes and Inefficient Antiviral Protection Are Rectified by Ubiquitination," J. Virol. 72:5174–5181 (1998).

Sambrook et al., Molecular Cloning: A Laboratory Manual, 2nd ed., pp. 16.6–16.15, Cold Spring Harbor Laboratory Press, New York, 1989.

Samulski et al., "Helper–Free Stocks of Recombinant Adeno–Associated Viruses, Normal Integration Does not Require Viral Gene Expression," J. Virol., 63, 3822–28, 1989.

Schlehofer et al., "Vaccinia Virus, Herpes Simplex Virus and Carcinogens Induce DNA Amplification in a Human Cell Line and Support Replication of A Helpervirus Dependent Parvovirus," Virol., 152, 110–117, 1986.

Schreiber et al., "Unique Tumor–Specific Antigens," Ann. Rev. Immunol. 6, 465–83, 1988.

Seth et al., "Mechanism of Enhancement of DNA Expression Consequent to Coininternalization of a Replication–Deficient Adenovirus and Unmodified Plasmid, DNA," J. Virol. 68, 933–40, 1994.

Shelling and Smith, "Targerted intergration of transfected and infected adeno–associated virus vectors containing the neomycin resistance gene," Gene Therapy, 1, 165–69, 1994.

Shigekawa et al., "Electroporation of Eukaryotes and Prokaryotes: A General Approach to the Indrocution of Macromolecules into Cells," BioTech, 6, 742–51, 1988.

Sikora, "Genetic Approaches to Cancer Therapy," Gene Therapy, 1, 149–51, 1994.

Spence et al., "Regulation of A bifunctional mRNA results in synthesis of secreted and nuclear probasin," Proc. Natl. Acad. Sci., USA, 86,7843–47, 1989.

Szomolanyi–Tsuda, et al., "T–Cell–Independent Immunoglobulin G Responses In Vivo Are Elicited by Live–Virus Infection but Not by Immunization with Viral Proteins or Virus–Like Particles," J. Virol. 72:6665–6670 (1998).

Thomson, et al., Human Herpesvirus 6 (HHV–6) is a Helper Virus for Adeno–Associated Virus Type 2 (AAV–2) and the AAV–2 rep Gene Homologue in HHV–6 Can Mediate AAV–2 DNA Replication and Regulate Gene Expression, Virol., 204, 304–11, 1994.

Tratschin et al., Experientia vol. 42, 695 (1986).

Tsuji et al., "Recombinant Sindbis Viruses Expressing a Cytotoxic T–Lymphocyte Epitope of a Malaria Parasite or of Influenza Virus Elicit Protection against the Corresponding Pathogen in Mice." J. Virol., 72:6907–6910 (1998).

Uetsuki et al., "Isolation and Characterzation of The Human Chromosomal Gene for Polypeptide Chain Elongation Factor–1a," J. Biol. Chem., 264,5791–98, 1989.

Ulmer, et al. "Protective CD4+ and CD8+ T Cells against Influenza Virus Induced by Vaccination with Nucleprotein DNA," J. Virol., 72:5648–5653 (1998).

Unanue et al., "The Basis for the Immunoregulatory Role of Macrophages and Other Accessory Cells," Science 236, 551–557, 1987.

Van Bruggen et. al, "Autoimmunity against nuclesomes and lupus nephritis," Ann. Med. Interne (Paris), 147, 485–89, 1996.

Verma et al., Science, vol. 389,239–242 (1997).

Verma and Somia, "Gene Therapy–promises, problems, prospects," Nature 389:239–242 (1997).

Vincent et al., "Replication and Packaging of HIV Envelope Genes in a Novel Adeno–associated Virus Vector Syste," Vaccines 90, 353–59, (Cold Spring Harbor Laboratory Press), 1990.

Voss et al., "The role of enhancers in the regulation of cell–type–specific transcriptional control." Trends Biochem Sci., 11, 287–89, 1986.

Warshaw et al., "Pancreatic Carcinoma," N. Engl. J. Med., 326, 455–465, 1992.

Wu and Wallace, "The Ligation Amplification Reaction (LAR)–Amplification of Specific DNA Sequences Using Sequential Rounds of Template Dependent Ligation," Geonomics, 4, 560–69, 1989.

Xiao et al., Exp. Neurol. vol. 144, 113–124, (1997).

Xiao et al., "Efficient Long–Term Gene Transfer Into Muscle Tissue of Immunocompetent Mice by Adeno–Associated Virus Vector," J. Virol. 70, 8098–8108, 1996.

Yang et al., "Immune Responses to Viral Antigens Versus Transgene product in the elimination of recombinant adenovirus–infected hepatocytes in vivo," Gene Therapy 3: 137–144 (1996).

Yang et al., "Cellular Immunity to Viral Antigens Limits E1–deleted Adenoviruses for gene therapy," Proc. Natl. Acad. Sci. 91: 4407–4411 (1994).

Yauch, et al, "Role of Individual T–Cell Epitopes of Theiler's Virus in Pathogenesis of Demyelination Correlates with the Ability to Induce a Th1 Response," J. Virol., 72: 6169–6174 (1998).

Young et al., Adeno–Associated Virus—an Extreme State of Viral Defectiveness, Prog. Med. Virol., 25, 113–32, 1979.

Zhou et al., "Adeno–associated Virus 2–mediated High Efficiency Gene Transfer into Immature and Matrue Subsets of Hematopoietic Progenitor Cells In Human Umbilical Cord Blood," J. Exp. Med., 179, 1867–75, 1994.

Bonnet, et al., "Recombinant Viruses as a Tool for Therapeutic Vaccination against Human Cancers," Immunology Letters 74 (2000) 11–25.

Coulie, et al., "A Monoclonal Cytolytic T–lymphocyte Response Observed in a Melanoma Patient Vaccinated with a Tumor–Specific Antigenic Peptide Encoded by Gene MAGE–3," PNAS, Aug. 28, 2001, vol. 98, No. 18, 10290–10295.

Eder, et al., "A Phase I Trial of a Recombinant Vaccinia Virus Expressing Prostate–specific Antigen in Advanced Prostate Cancer," Clinical Cancer Research, vol. 6, 1632–1638 (May 2000).

Abstract of Khleif, et al., "A Phase I Vaccine Trial with Peptides Reflecting Ras Oncogene Mutations of Solid Tumors," PubMed, J Immunother (Mar. 1999) 22(2): 155–65.

Gulley, et al., "Phase I Study of a Vaccine Using Recombinant Vaccinia Virus Expressing PSA (rV–PSA) in Patients With Metastatic Androgen–Independent Prostate Cancer," The Prostate (2002) 53: 109–117.

Johnen, et al., "Long–term Tumor Growth Supression in Mice Immunized with Naked DNA of the Human Tumor Antigen Mucin (MUC1)," Cancer Immunol Immunother (2001) 50: 356–360.

Ben–Hur, et al., "Tumor–Preventive Effects of the Soluble p53 Antigen on Chemically–Induced Skin Cancer in Mice," Anticancer Research 18: 4237–4242 (1998).

Berinstein, N., "Carcinoembryonic Antigen as a Target for Therapeutic Anticancer Vaccines: A Review," Journal of Clinical Oncology, vol. 20, No. 8 (Apr. 15, 2000) 2197–2207.

White, et al., "Induction of Anti–Tumor Immunity by Intrasplenic Administration of a Carcineombryonic Antigen DNA Vaccine," The Journal of Gene Medicine, J Gene Med (2000) 2: 135–140.

* cited by examiner

INDUCTION OF IMMUNE RESPONSE TO ANTIGENS EXPRESSED BY RECOMBINANT ADENO-ASSOCIATED VIRUS

This application is a continuation of Ser. No. 09/121,162, filed Jul. 23, 1998, now U.S. Pat. No. 6,242,426, and claims priority benefit of U.S. provisional application No. 60/053,733, filed Jul. 25, 1997, pending, which is hereby incorporated herein by reference in its entirety.

This invention was funded in part by grants CA71725, HL57443, and CA72103 from the National Institutes of Health. The U.S. Government has certain rights in this invention.

FIELD OF THE INVENTION

The present invention relates generally to immunization methods using recombinant viral vectors. In particular, the invention relates to methods and compositions for immunizing a subject with a nucleic acid molecule encoding an antigen of interest, wherein the nucleic acid molecule is delivered to the subject via a recombinant AAV vector.

BACKGROUND

Ever since the first experiments in variolation in 1721, and Jenner's vaccination methods in 1796, methods and compositions for disease prevention utilizing immunization have been extensively investigated. Many methods rely upon the use of active immunization, in which an antigen (or mixtures of antigens), such as a modified infectious agent or toxin is administered, resulting in active immunity. This active immunity is characterized by the production of antibodies directed against the administered antigen(s), and in some cases, induction of cellular responses mediated by lymphocytes and macrophages.

Traditionally, vaccines used for active immunization have consisted of live attenuated bacteria (e.g., Bacillus Calmette-Guérin) or viruses (e.g., measles virus), killed microorganisms (e.g., *Vibrio cholerae*), inactivated bacterial products (e.g., tetanus toxoid), or specific single components of bacteria (e.g., *Haemophilus influenzae* polysaccharide). Although active immunization with live organisms is generally superior to immunization with killed vaccines in producing long-lived immune responses, care must be taken to properly store and administer these vaccines, as serious failures of measles and smallpox immunizations have resulted from improper refrigeration of the vaccine preparations. In addition, pregnant women and individuals with compromised immune systems should, in general, not receive live vaccines, as the organisms may cause serious disease upon vaccination. For example, live vaccines have caused serious and fatal disease in patients receiving corticosteroids, alkylating drugs, radiation, other immunosuppressive treatments, as well as individuals with known or suspected congenital or acquired defects in cell-mediated immunity (e.g., severe combined immunodeficiency disease, leukemia, lymphoma, Hodgkin's disease, and acquired immunodeficiency syndrome [AIDS]). Live vaccines may even cause mild, or rarely, severe disease in immunocompetent hosts. In addition, live vaccines may also contain undesirable components. For example, epidemic hepatitis has resulted from the use of vaccinia and yellow fever vaccines containing human serum.

Passive immunization using preformed immunoreactive serum or cells is sometimes utilized, especially when active immunization is not available or not advisable. In particular, passive immunization finds use in individuals who cannot produce antibodies or other immune system deficiencies, as well as in individuals who are at risk of developing disease before active immunization would be successful in stimulating a sufficient antibody response. Passive immunization is also used in conjunction with vaccine administration in the management of certain diseases (e.g., rabies vaccination and prophylaxis following an animal bite), management of individuals who have been exposed to certain toxins or venoms, and as an immunosuppressant. However, passive immunization does not produce long-term immunity and is sometimes associated with severe reactions due to the presence of foreign proteins in the vaccine preparation (e.g., anaphylaxis resulting from a reaction against human or horse [or other non-human animal] proteins present in the vaccine preparation).

More recently, vaccines comprising recombinant DNA or RNA segments have been developed. However, use of these recombinant vaccines has resulted in problems associated with the expression of the desired antigen(s) in another organism (e.g., an *E. coli* or yeast host). For example, in addition to the desired antigen, other components, such as other antigens (e.g., protein and other components) from the expression host, preservatives, etc may be present in the preparation. In addition, adjuvants are sometimes required in order to provide efficacious vaccination with these vaccines. However as with passive immunization, undesirable reactions sometimes occur in vaccinated individuals due to the presence of these undesirable components.

Various adenovirus-based gene delivery systems have likewise been investigated for vaccine use. Human adenoviruses are double-stranded DNA viruses which enter cells by receptor-mediated endocytosis. These viruses have been viewed as being particularly well suited for gene transfer because they are easy to grow and manipulate and they exhibit a broad host range in vivo and in vitro. Adenovirus is easily produced at high titers and is stable so that it can be purified and stored. Even in the replication-competent form, adenoviruses generally cause only low level morbidity and are not associated with human malignancies. Various references provide reviews of adenovirus-based gene delivery systems (See, e.g., Haj-Ahmad and Graham, *J. Virol.*, 57:267–274 [1986]; Bett et al., *J. Virol.*, 67:5911–5921 [1993]; Mittereder et al., *Human Gene Ther.*, 5:717–729 [1994]; Seth et al., *J. Virol.*, 68:933–940 [1994]; Barr et al., *Gene Ther.*, 1:51–58 [1994]; Berkner, *BioTechn.*, 6:616–629 [1988]; and Rich et al., *Human Gene Ther.*, 4:461–476 [1993]). However, despite these advantages, adenovirus vector systems still have several drawbacks which limit their effectiveness in gene delivery, such as cytotoxicity. Adenovirus vectors also express viral proteins that may elicit a strong non-specific immune response in the host. This non-specific immune reaction may increase toxicity or preclude subsequent treatments because of humoral and/or T cell responses against the adenoviral particles. Thus, problems remain even with the newer technologies for vaccine administration.

As briefly mentioned above, the major focus in the past has been on the development of antibody responses to vaccination. However, cell-mediated responses are of great importance in some situations. Indeed, cell-mediated immunity is of greater importance than the antibody-mediated response in the response to intracellular parasites (e.g., viruses and obligately intracellular bacteria). T-cells (T lymphocytes) play the primary roles in cell-mediated immunity, although there is communication via cytokines and other signalling compounds between these cells as the antibody-producing B-cells.

Cytotoxic T-lymphocytes (CTLs) play an important role in immune responses directed against intracellular pathogens such as viruses and tumor-specific antigens produced by cancerous cells. In particular, CTLs mediate cytotoxicity of virally infected cells by recognizing viral determinants in conjunction with Class I MHC molecules displayed by the infected cells. Cytoplasmic expression of proteins is a prerequisite for Class I MHC processing and presentation of antigenic peptides to CTLs. However, conventional immunization techniques, such as those using killed or attenuated viruses, often fail to elicit an appropriate CTL response which is effective against an intracellular infection. Thus, there remains a need for the development of vaccines that stimulate appropriate responses (i.e., cell-mediated as well as antibody-mediated immune responses), in order to prevent disease. Indeed, despite advances in vaccine technology, there remains a need for vaccines that are efficacious, yet avoid the problems associated with current vaccine preparations.

SUMMARY

The present invention relates generally to immunization methods using recombinant viral vectors. In particular, the invention relates to methods and compositions for immunizing a subject with a nucleic acid molecule encoding an antigen of interest, wherein the nucleic acid molecule is delivered to the subject via a recombinant AAV vector.

The present invention provides a method of eliciting an immune response in a subject, comprising the steps of: providing a recombinant AAV vector containing a nucleic acid molecule encoding at least one antigen of interest operably linked to control sequences which direct the expression of the antigen of interest in a suitable recipient cell; and introducing the recombinant AAV vector into a recipient cell of the subject under conditions that permit the expression of the one or more antigen, thereby eliciting an immune response to the antigen of interest. In some embodiments, the recombinant AAV vector comprises a recombinant AAV virion.

In some embodiments of the present invention, the immune response comprises production of cytotoxic T lymphocytes directed against the antigen of interest. In other embodiments, the immune response comprises production of antibodies directed against the antigen of interest. In yet other embodiments, the immune response comprises production of interleukin-2 and gamma interferon. In preferred embodiments, the immune response is a $T_H1$-like response.

In some embodiments of the present invention, the immune response comprises the production of one or more cytokines selected from the group consisting of interleukin-4, interleukin-5, interleukin-10, and interleukin-13. In preferred embodiments, the immune response is a $T_H2$-like response.

In other embodiments, the antigen of interest comprises at least one antigen selected from the group consisting of tumor antigens, viral antigens, bacterial antigens, and protozoal antigens. In other embodiments, the antigen of interest is derived from an intracellular pathogen. In alternative embodiments, the antigen of interest is a self-antigen. In yet other embodiments, the antigen of interest is an allergen.

In some embodiments, the expression of the antigen of interest persists for approximately eight weeks after the introducing of the antigen of interest to the recipient cell of the subject. In preferred embodiments, the expression of the antigen of interest persists for at least eight weeks after introducing the antigen of interest to the recipient cell of the subject.

The present invention further provides a method for shifting the cytokine profile of an immune response against an antigen in a subject, comprising the steps of: providing a recombinant AAV vector containing a nucleic acid molecule encoding at least one antigen of interest operably linked to control sequences which direct the expression of the antigen of interest in a suitable recipient cell; and introducing the recombinant AAV vector into a recipient cell of the subject under conditions that permit the expression of the antigen, thereby eliciting a desensitizing immune response specific for the antigen. In some embodiments, the antigen is an allergen. In preferred embodiments, the shifting in the immune response is characterized by a switch from a $T_H1$-like response to a $T_H2$-like response.

The present invention also provides a method for treating or preventing an autoimmune disease in a vertebrate subject, said method comprising: providing a recombinant AAV vector containing a nucleic acid molecule encoding an antigen against which an immune response is mounted in the autoimmune disease, wherein the nucleic acid molecule is operably linked to control sequences which direct the expression thereof in a suitable recipient cell; and introducing the AAV vector into a recipient cell of the vertebrate subject under conditions that permit the expression of the antigen in an amount sufficient to bring about a reduction in a cytotoxic immune response or a desensitizing immune response against the antigen. In some embodiments, the recombinant AAV vector comprises a recombinant AAV virion.

The present invention further provides a method for modulating allergic reaction in a vertebrate subject, said method comprising: providing an AAV vector containing a nucleic acid molecule encoding an immunogenic molecule having a first portion derived from an IgE molecule and a second portion derived from an immunogenic carrier molecule, wherein the nucleic acid molecule is operably linked to control sequences which direct the expression thereof in a suitable recipient cell; and introducing the AAV vector into a recipient cell of the vertebrate subject under conditions that permit the expression of the immunogenic molecule, thereby eliciting an immune response against IgE molecules in the vertebrate subject. In some embodiments, the recombinant AAV vector comprises a recombinant AAV virion.

The present invention also provides an in vitro target system for monitoring an immune response to an antigen of interest in a vertebrate sample, said system comprising a population of target cells transduced with an AAV vector containing a nucleic acid molecule encoding the antigen of interest operably linked to control sequences which direct the expression thereof in the target cell, wherein the target cell is capable of presenting the antigen of interest associated with a MHC class I molecule.

These and other embodiments of the invention will readily occur to those of ordinary skill in the art in view of the disclosure herein.

BRIEF DESCRIPTION OF THE DRAWINGS

FIGS. 1A–1B depict the construction of the recombinant AAV virions rAAV-Ova (containing the cDNA encoding ovalbumin) and rAAV-LacZ (containing the cDNA encoding β-galactosidase from *E. coli*).

FIGS. 2A–2B depict ELISA results demonstrating that administration of rAAV-Ova in vivo induces an ovalbumin-specific humoral response.

FIGS. 3A–3E depict results from experiments in which rAAV-Ova induced antigen-specific CTL was introduced into C57BL/6 mice injected with $3 \times 10^{11}$ rAAV-Ova virions (3A, 3B, 3C, 3D) or $3 \times 10^{11}$ rAAV-lacZ virions (3E).

FIGS. 4A–4C depict results showing that antigen-presenting cells transduced with rAAV-Ova stimulate a $CD8^+$, MHC Class I-restricted T cell hybridoma.

GENERAL DESCRIPTION OF THE INVENTION

The present invention relates generally to immunization methods using recombinant viral vectors. In particular, the invention relates to methods and compositions for immunizing a subject with a nucleic acid molecule encoding an antigen of interest, wherein the nucleic acid molecule is delivered to the subject via a recombinant AAV vector.

Unless otherwise indicated, the practice of the present invention employs conventional methods of virology, microbiology, molecular biology and recombinant DNA techniques within the skill of the art, including those described in such references as Sambrook et al. (eds.) *Molecular Cloning: A Laboratory Manual*; Glover (ed.) *DNA Cloning: A Practical Approach*, Vols. I & II; Gait (ed.) *Oligonucleotide Synthesis*; Hames and Higgins (eds.) *Nucleic Acid Hybridization*; Hames and Higgins (eds.) *Transcription and Translation*; Tijessen (ed.) *CRC Handbook of Parvoviruses*, Vols. I & II; and Fields and Knipe (eds.) *Fundamental Virology*, 2nd Edition, Vols. I & II.

Adeno-associated Viruses (AAV)

Adeno-associated virus (AAV) is a non-pathogenic, replication-defective, helper-dependent parvovirus (or "dependovirus," or "adeno-satellite virus"). There are at least six recognized serotypes, designated as AAV-1, AAV-2, AAV-3, and AAV-4, AAV-5, AAV-X7, etc. Serologic evidence has indicated that AAV-1 may have originated from rhesus monkeys, and AAV-4 probably originated from green monkeys, while both culture and serologic evidence indicates that human infection occurs with AAV-2 and AAV-3 (Lang, in *Principles of Animal Virology*[W. K. Joklik, ed], Appleton-Century-Crofts, New York [1980], at page 255). Although 85% of the human population is seropositive for AAV-2, the virus has never been associated with disease in humans (Bems et al., *Adv. Virus Res.*, 32:243–306 [1987]). Recombinant AAV (rAAV) virions are of interest as vectors for vaccine preparations and gene therapy because of their broad host range, excellent safety profile, and duration of transgene expression in infected hosts. One remarkable feature of recombinant AAV (rAAV) virions is the prolonged expression achieved after in vivo administration (Fisher et al., *Nat. Med.*, 3:306–312 [1997]; Flotte et al., *Proc. Natl. Acad. Sci. USA* 90:10613–10617 [1993]; and Xiao et al., *J. Virol.*, 70:8098–8108 [1996]). Indeed, prior to the development of the present invention, this property was thought to limit the immunotherapeutic applications of rAAV virions. However, the present invention provides compositions and methods for eliciting immunity to a foreign transgene product in vivo using rAAV.

The present invention is particularly suited for use in vaccine preparations and methods. For example, in contrast to the prior art, the present invention provides rAAV virions encoding a different foreign transgene (e.g., ovalbumin) that has been shown to be capable of eliciting both cellular and immune responses upon introduction into an animal. Although an understanding of the mechanism is not necessary in order to use the present invention, it is thought that perhaps the viral dose correlates with antigen presentation and raises the possibility that there is a threshold of transgene expression required for the induction of CTL in vivo, a threshold that is met by the present invention.

Again, although an understanding of the mechanism is not necessary in order to use the present invention, and it is not intended that the present invention be limited to any particular route of administration, it is hypothesized that the route of AAV vaccine administration might also play an important role in eliciting an immune response. For example, data presented in the Examples suggest that at least in some cases, the subcutaneous (SC) and the intravenous (IV) routes might be more efficient in inducing antigen-specific CTL than the intramuscular (IM) route used in the earlier studies. The lower immunogenicity of rAAV after IM administration might contribute to the long-term expression of the transgene product in muscle reported by several groups. Regardless of the previous failure to elicit immunity with rAAV, the results obtained during the development of the present invention clearly demonstrate that rAAV-Ova transduction results in entry of ovalbumin into the classical, TAP-2 dependent MHC Class I processing pathway in vitro, and in the formation of ovalbumin-specific CTL and antibodies in vivo. Since AAV has not been associated with human disease, despite evidence of widespread infection, and since rAAV appears to be a safe and efficient vector in animal models, the present invention provides compositions and methods that will find use in inducing protective immunity to viral infections, tumors, and/or intracellular pathogens.

Accordingly, in one embodiment of the invention, methods are provided for eliciting an immune response in a subject. The methods include providing an AAV vector containing a nucleic acid molecule encoding an antigen of interest operably linked to control sequences that direct expression of the antigen in a suitable recipient cell. The AAV vector is introduced into a recipient cell of the subject, under conditions allowing expression of the antigen, thereby eliciting an immune response against the antigen. In various embodiments of the methods, the AAV vector is comprised of a recombinant AAV (rAAV) virions. In other embodiments, the AAV vector contains a gene that encodes a tumor-specific antigen, a viral antigen, a bacterial antigen, a protozoal antigen, and/or any intracellular parasite antigen. The AAV vector can be administered to the subject in vivo using any suitable route of administration, including but not limited to intramuscular, intravenous, intraperitoneal, subdermal, intradermal, intraocular, or subcutaneous injection techniques. In one embodiment, immunization is carried out using a single injection of the AAV vector.

The present invention also provides methods for shifting the cytokine profile of a subject's immune response against an antigen. In one embodiment, an AAV vector containing a nucleic acid molecule encoding the antigen is introduced into a recipient cell of the subject, under conditions that permit the expression of the antigen. This antigen expression elicits a desensitizing immune response specific for the antigen. In related embodiments of the invention, the antigen is an allergen, and/or the shift in the immune response is characterized by a switch from a $T_H1$-like response to a $T_H2$-like response.

The present invention also provides methods for treating or preventing an autoimmune disease in a subject. In one embodiment, the method comprises providing an AAV vector containing a nucleic acid molecule encoding an antigen against which an immune response is mounted in the autoimmune disease, and introducing the AAV vector into a recipient cell of a subject, under conditions that permit the expression of the antigen in the recipient cell. The antigen is expressed in an amount sufficient to bring about a reduction in a cytotoxic immune response or a desensitizing immune response against the antigen.

The present invention also provides methods for modulating allergic reaction(s) in a subject. In some embodiments, these method include the steps of providing an AAV vector containing a nucleic acid molecule encoding an immunogenic molecule having a first portion derived from an IgE molecule and a second portion derived from an immunogenic carrier molecule, wherein the nucleic acid molecule is operably linked to control sequences which direct the expression the immunogenic molecule in a suitable recipient cell. The AAV vector is introduced into a recipient cell of a subject under conditions that permit the expression of the immunogenic molecule to elicit an immune response against IgE molecules.

The present invention also provides target cell systems useful for monitoring and/or assessing an immune response in an AAV-immunized subject in preferred embodiments. The target systems comprise a population of recipient cells transduced with an AAV vector encoding an antigen of interest. The cells are capable of processing the antigen of interest using the Class I MHC pathway, and presenting the antigen in association with a MHC Class I molecule. These systems provide a well-defined target system with which to monitor or detect an antigen-specific immune response in a subject immunized with an AAV vector using the methods of the present invention. In addition, the transduced cells can be used in T cell proliferation assays, CTL assays (e.g, chromium release assays), antibody binding assays, antibody-dependent cell-mediated cytotoxicity (ADCC) assays, and any other suitable assay system.

Antibody Production

The present invention also provides methods for producing antibodies directed against an antigen of interest that is contained in an AAV vaccine preparation. In these methods, an animal having immunocompetent cells is exposed to an immunogen comprising at least an immunogenic portion of the antigen of interest, under conditions such that immunocompetent cells produce antibodies directed against the immunogenic portion(s) of the immunogen. In one embodiment, the method further comprises the step of harvesting the antibodies. In an alternative embodiment, the method comprises the step of fusing the immunocompetent cells with an immortal cell line under conditions such that an hybridoma is produced. In other embodiments, the immunogen comprises a fusion protein.

The present invention also provides methods for detecting antigen or immunogen expression comprising the steps of: a) providing a sample suspected of containing the antigen of interest and a control containing a quantitated amount of known antigen; and b) comparing the test antigen in the sample with the quantitated known antigen in the control to determine the relative concentration of the test antigen in the sample. Thus, the methods are capable of identifying samples (e.g., patient samples) with sufficient or insufficient quantities of antigen of interest, providing an indication of the strength of the expected immune response by the patient against the antigen. In addition, the methods may be conducted using any suitable means to determine the relative concentration of the antigen of interest in the test and control samples, including but not limited to means selected from the group consisting of Western blot analysis, Northern blot analysis, Southern blot analysis, denaturing polyacrylamide gel electrophoresis, reverse transcriptase-coupled polymerase chain reaction, enzyme-linked immunosorbent assay, radioimmunoassay, and fluorescent immunoassay. Thus, the methods may be conducted to determine the presence of the antigen of interest in the genome of the animal source of the test sample, or the expression of the antigen of interest (MRNA or protein), as well as detect the presence of abnormal or mutated antigen or antigen gene sequences in the test samples.

In one preferred embodiment, the presence of the antigen of interest is detected by immunochemical analysis. For example, the immunochemical analysis can comprise detecting binding of an antibody specific for an epitope of the antigen of interest. In an another preferred embodiment of the method, the antibody comprises polyclonal antibodies, while in another preferred embodiment, the antibody comprises monoclonal antibodies.

The antibodies used in the methods of the present invention may be prepared using various immunogens. In one embodiment, the immunogen is an antigen of interest used as an immunogen to generate antibodies that recognize the antigen of interest. Such antibodies include, but are not limited to polyclonal, monoclonal, chimeric, single chain, Fab fragments, and an Fab expression library.

Various procedures known in the art may be used for the production of polyclonal antibodies to the antigen of interest encoded by the AAV vaccine preparation. For example, for the production of antibody, various host animals can be immunized by injection with a peptide corresponding to at least one epitope of the antigen of interest, including but not limited to rabbits, mice, rats, sheep, goats, etc. In some embodiments, the peptide is conjugated to an immunogenic carrier (e.g., diphtheria toxoid, bovine serum albumin [BSA], or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guérin) and *Corynebacterium parvum*.

For preparation of monoclonal antibodies directed toward an antigen of interest, any technique that provides for the production of antibody molecules by continuous cell lines in culture may be used (See, e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, *Nature* 256:495–497 [1975]), as well as the trioma technique, the human B-cell hybridoma technique (See e.g., Kozbor et al. *Immunol. Today* 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., *Proc. Natl. Acad. Sci. USA* 80:2026–2030 [1983]) or by transforming human B cells with EBV virus in vitro (Cole et al., in *Monoclonal Antibodies and Cancer Therapy*, Alan R. Liss, pp. 77–96 [1985]).

According to the invention, techniques described for the production of single chain antibodies (U.S. Pat. No. 4,946,778; herein incorporated by reference) can be adapted to produce single chain antibodies useful in embodiments of the present invention. An additional embodiment of the present invention utilizes the techniques described for the construction of Fab expression libraries (Huse et al., *Science* 246:1275–1281 [1989]), to allow rapid and easy identification of monoclonal Fab fragments with the desired specificity.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art including, but not limited to, radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay).

The foregoing antibodies can be used in methods known in the art relating to the localization and structure of the antigen of interest (e.g., for Western blotting), measuring levels thereof in appropriate biological samples, etc. The antibodies can be used to detect the antigen of interest in a biological sample from an individual. The biological sample can be a biological fluid, including, but not limited to, blood, serum, plasma, interstitial fluid, urine, cerebrospinal fluid, and the like, containing cells. In particular, the antigen can be detected from cellular sources, including, but not limited to, platelets and fibroblasts. For example, platelets or fibroblasts can be obtained from an individual and lysed (e.g. by freeze-thaw cycling, or treatment with a mild cytolytic detergent including, but not limited to, TRITON X-100, digitonin, NONIDET P (NP)-40, saponin, and the like, or combinations thereof; See, e.g., International Patent Publication WO 92/08981).

The biological samples can then be tested directly for the presence of the antigen of interest using an appropriate strategy (e.g., ELISA or radioimmunoassay) and format (e.g., microwells, dipstick [e.g., as described in International Patent Publication WO 93/03367], etc.). Alternatively, proteins in the sample can be size separated (e.g., by polyacrylamide gel electrophoresis (PAGE), in the presence or not of sodium dodecyl sulfate (SDS), and the presence of the antigen of interest detected by immunoblotting (e.g., Western blotting)). Immunoblotting techniques are generally more effective with antibodies generated against a peptide corresponding to an epitope of a protein, and hence, are particularly suited to the present invention.

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

Definitions

In describing the present invention, the following terms will be employed, and are intended to be defined as indicated below.

As used herein, the terms "gene transfer" and "gene delivery" refer to methods or systems for reliably inserting a particular nucleotide sequence (e.g., DNA) into targeted cells.

As used herein, the terms "vector," and "gene transfer vector" refer to any genetic element, such as a plasmid, phage, transposon, cosmid, chromosome, virus, virion, etc., which is capable of replication when associated with the proper control elements and/or which can transfer nucleic acid sequences between cells. Thus, the term includes cloning and expression vehicles, as well as viral vectors.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, as well as other sequences. Eukaryotic cells are known to utilize promoters, enhancers, and termination and polyadenylation signals.

It is contemplated that gene transfer vectors constructed using recombinant techniques that are known in the art to include a nucleic acid sequence encoding an antigen associated with functional AAV ITR sequences will find use in the present invention. In addition, the present invention contemplates gene transfer vectors that contain suitable promoter sequence positioned upstream of a heterologous nucleotide sequence encoding an antigen of interest.

Gene transfer vectors can also include transcription sequences such as polyadenylation sites, as well as selectable markers or reporter genes, enhancer sequences, and other control elements which allow for the induction of transcription. Such control elements are described more fully below.

As used herein, the terms "host" and "expression host" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the terms "viral replicons" and "viral origins of replication" refer to viral DNA sequences that allow for the extrachromosomal replication of a vector in a host cell expressing the appropriate replication factors. In some embodiments, vectors which contain either the SV40 or polyoma virus origin of replication replicate to high copy number (up to $10^4$ copies/cell) in cells that express the appropriate viral T antigen may be utilized, while vectors which contain the replicons from bovine papillomavirus or Epstein-Barr virus replicate extrachromosomally at low copy number (~100 copies/cell) may be utilized in other embodiments.

As used herein, the term "AAV vector" refers to a vector derived from an adeno-associated virus serotype, including without limitation, AAV-1, AAV-2, AAV-3, AAV-4, AAV-5, AAV-X7, etc. AAV vectors can have one or more of the AAV wild-type genes deleted in whole or part, preferably the rep and/or cap genes but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides), so long as the sequences provide for functional rescue, replication and packaging.

As used herein, the term "ITR" refers to inverted terminal repeats. The terms "adeno-associated virus inverted terminal repeats" or "AAV ITRs" refer to the art-recognized palindromic regions found at each end of the AAV genome which function together in cis as origins of DNA replication and as packaging signals for the virus. For use in some embodiments of the present invention, flanking AAV ITRs are positioned 5' and 3' of one or more selected heterologous nucleotide sequences and, together with the rep coding region or the Rep expression product, provide for the integration of the selected sequences into the genome of a target cell. These sequences, located at the terminal ends of the viral genome, function in cis as origins of DNA replication and as packaging signals for the virus.

As used herein, the term "AAV rep coding region" refers to the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Muzyckza (Muzyczka, *Curr. Top. Microbiol. Immunol.*, 158:97–129 [1992]) and Kotin (Kotin, *Human Gene Ther.*, 5:793–801 [1994]) provide additional descriptions of the AAV rep coding region, as well as the cap coding region described below. Suitable homologues of the AAV rep coding region include the human herpesvirus 6 (HHV-6) rep gene which is also known to mediate AAV-2 DNA replication (Thomson et al., *Virol.*, 204:304–311 [1994]).

As used herein, the term "AAV cap coding region" refers to the art-recognized region of the AAV genome which encodes the capsid proteins VP1, VP2, and VP3, or functional homologues thereof. These cap expression products supply the packaging functions which are collectively required for packaging the viral genome.

As used herein, the terms "accessory functions" and "accessory factors" refer to functions and factors that are required by AAV for replication, but are not provided by the AAV virion (or rAAV virion) itself. Thus, these accessory functions and factors must be provided by the host cell or another expression vector that is co-expressed in the same cell.

As used herein, the term "wild type" ("wt") refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "AAV virion" refers to a complete virus particle, such as a "wild-type" (wt) AAV virus particle (comprising a linear, single-stranded AAV nucleic acid genome associated with an AAV capsid protein coat). In this regard, single-stranded AAV nucleic acid molecules of either complementary sense (e.g., "sense" or "antisense" strands), can be packaged into any one AAV virion and both strands are equally infectious.

As used herein, the terms "recombinant AAV virion," and "rAAV virion" refer to as an infectious viral particle containing a heterologous DNA molecule of interest which is flanked on both sides by AAV ITRs. In some embodiments of the present invention, an rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into recombinant virion particles for subsequent gene delivery.

As used herein, the term "recombinant AAV vector" refers a composition comprising an AAV vector comprising one or more heterologous DNA molecules of interest. As described above, AAV vectors can have one or more of the AAV wild-type elements deleted in whole or in part. Thus, in one embodiment, a recombinant AAV vector comprises a heterologous DNA molecule of interest which is flanked on both sides by AAV ITRs. In other embodiments, the recombinant AAV vector may further comprise elements required for viral infection (e.g., an AAV protein shell). In such embodiments, the "recombinant AAV vector" may comprise a recombinant AAV virion.

As used herein, the term "transfection" refers to the uptake of foreign DNA by a cell, and a cell has been "transfected" when exogenous DNA has been introduced inside the cell membrane. A number of transfection techniques are generally known in the art (See e.g., Graham et al., *Virol.*, 52:456 [1973]; Sambrook et al., *Molecular Cloning, a Laboratory Manual*, Cold Spring Harbor Laboratories, New York [1989]; Davis et al., *Basic Methods in Molecular Biology*, Elsevier, [1986]; and Chu et al., *Gene* 13:197 [1981]. Such techniques can be used to introduce one or more exogenous DNA moieties, such as a gene transfer vector and other nucleic acid molecules, into suitable recipient cells.

As used herein, the terms "stable transfection" and "stably transfected" refers to the introduction and integration of foreign DNA into the genome of the transfected cell. The term "stable transfectant" refers to a cell which has stably integrated foreign DNA into the genomic DNA.

As used herein, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "transduction" denotes the delivery of a DNA molecule to a recipient cell either in vivo or in vitro, via a replication-defective viral vector, such as via a recombinant AAV virion.

As used herein, the term "recipient cell" refers to a cell which has been transfected or transduced, or is capable of being transfected or transduced, by a nucleic acid construct or vector bearing a selected nucleotide sequence of interest. The term includes the progeny of the parent cell, whether or not the progeny are identical in morphology or in genetic make-up to the original parent, so long as the selected nucleotide sequence is present.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transfected with a construct which is not normally present in the cell would be considered heterologous for purposes of this invention. Allelic variation or naturally occurring mutational events do not give rise to heterologous DNA, as used herein.

As used herein, "coding sequence" or a sequence which "encodes" a particular antigen, is a nucleic acid sequence which is transcribed (in the case of DNA) and translated (in the case of mRNA) into a polypeptide in vitro or in vivo, when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, the term "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the terms "complementary" or "complementarity" are used in reference to polynucleotides (i.e., a sequence of nucleotides) related by the base-pairing rules. For example, for the sequence "A—G—T," is complementary to the sequence "T—C—A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, the term "antisense" is used in reference to nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate recipient cell.

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (See e.g., Voss et al., Trends Biochem. Sci., 11:287 [1986]; and Maniatis et al., supra, for reviews). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]). Thus, it is not intended that the present invention be limited to AAV-derived promoters or other control elements.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook et al., supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. For example, vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes;

RNA sequences, such as a specific mRNA sequence encoding a specific protein, are found in the cell as a mixture with numerous other mRNAs which encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "purified" or "to purify" refers to the removal of contaminants from a sample. For example, antibodies may be purified by removal of contaminating non-immunoglobulin proteins; they may also purified by the removal of immunoglobulin that does not bind the antigen of interest. The removal of non-immunoglobulin proteins and/or the removal of immunoglobulins that do not bind the antigen of interest results in an increase in the percent of desired antigen-reactive immunoglobulins in the sample. In another example, recombinant polypeptides of interest are expressed in bacterial host cells and the polypeptides are purified by the removal of host cell proteins; the percent of recombinant polypeptides is thereby increased in the sample.

An "immune response" to an antigen is the development in a mammalian subject of a humoral and/or a cellular immune response to the antigen of interest. A "cellular immune response" is one mediated by T lymphocytes and/or other white blood cells. One important aspect of cellular immunity involves an antigen-specific response by cytotoxic T lymphocytes ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes.

As used herein, the term "antigen" refers to any agent (e.g., any substance, compound, molecule [including macromolecules], or other moiety), that is recognized by an antibody, while the term "immunogen" refers to any agent (e.g., any substance, compound, molecule [including macromolecules], or other moiety) that can elicit an immunological response in an individual. These terms may be used to refer to an individual macromolecule or to a homogeneous or heterogeneous population of antigenic macromolecules. It is intended that the term encompasses protein molecules or at least one portion of a protein molecule, which contains one or more epitopes. In many cases, antigens are also immunogens, thus the term "antigen" is often used interchangeably with the term "immunogen." The substance may then be used as an antigen in an assay to detect the presence of appropriate antibodies in the serum of the immunized animal.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

The term "monovalent" when used in reference to a vaccine refers to a vaccine which is capable of provoking an immune response in a host animal directed against a single type of antigen. In contrast, a "multivalent" vaccine provokes an immune response in a host animal directed against several (i.e., more than one) toxins and/or enzymes associated with disease (e.g., glycoprotease and/or neuraminidase). It is not intended that the vaccine be limited to any particular organism or immunogen.

The present invention further contemplates immunization with or without adjuvant. As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. It is contemplated that adjuvants may be used either separately or in combination. The present invention contemplates all types of adjuvant, including but not limited to agar beads, aluminum hydroxide or phosphate (alum), Incomplete Freund's Adjuvant, as well as Quil A adjuvant commercially available from Accurate Chemical and Scientific Corporation, Gerbu adjuvant also commercially available (GmDP; C.C. Biotech Corp.), and bacterin (i.e., killed preparations of bacterial cells). It is further contemplated that the vaccine comprise at least one "excipient" (i.e., a pharmaceutically acceptable carrier or substance) suitable for administration to a human or other animal subject. It is intended that the term "excipient" encompass liquids, as well as solids, and colloidal suspensions.

As used herein the term "immunogenically-effective amount" refers to that amount of an immunogen required to invoke the production of protective levels of antibodies in a host upon vaccination.

The term "protective level," when used in reference to the level of antibodies induced upon immunization of the host with an immunogen means a level of circulating antibodies sufficient to protect the host from challenge with a lethal dose of the organism or other antigenic material (e.g., toxins, etc.).

A "B cell epitope" generally refers to the site on an antigen to which a specific antibody molecule binds. The identification of epitopes which are able to elicit an antibody response is readily accomplished using techniques well known in the art (See e.g., Geysen et al. *Proc. Natl. Acad. Sci. USA* 81:3998–4002 [1984], for general method of rapidly synthesizing peptides to determine the location of immunogenic epitopes in a given antigen; U.S. Pat. No. 4,708,871 for procedures for identifying and chemically synthesizing epitopes of antigens; and Geysen et al., *Mol. Immunol.*, 23:709–715 [1986] for a technique for identifying peptides with high affinity for a given antibody).

A "T cell epitope" refers generally to those features of a peptide structure capable of inducing a T cell response. In this regard, it is accepted in the art that T cell epitopes comprise linear peptide determinants that assume extended conformations within the peptide-binding cleft of MHC molecules, (See, Unanue et al., *Science* 236:551–557 [1987]). As used here, a T cell epitope is generally a peptide having about 3–5, preferably 5–10 or more, amino acid residues.

The term "self antigen" or "autoantigen," means an antigen or a molecule capable of being recognized during an immune response as self (i.e., an antigen that is normally part of the individual). This is in contrast to antigens which are foreign, or exogenous, and are thus not normally part of the individual's antigenic makeup.

As used herein, the term "autoimmune disease" means a set of sustained organ-specific or systemic clinical symptoms and signs associated with altered immune homeostasis that is manifested by qualitative and/or quantitative defects of expressed autoimmune repertoires. Autoimmune diseases are characterized by antibody or cytotoxic immune responses to epitopes on self antigens found in the diseased individual. The immune system of the individual then activates an inflammatory cascade aimed at cells and tissues presenting those specific self antigens. The destruction of the antigen, tissue, cell type, or organ attacked by the individual's own immune system gives rise to the symptoms of the disease. Clinically significant autoimmune diseases include, for example, rheumatoid arthritis, multiple sclerosis, juvenile-onset diabetes, systemic lupus erythematosus (SLE), autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura.

As used herein, the term "anergy" means a reversible antiproliferative state which results in decreased responsiveness of an immune cell or cells to an antigen. "T-cell anergy" refers to anergy of at least one T-cell population. For example, T-cell anergy is involved in deviation of specific immunity from a $T_H1$-like to a $T_H2$-like immune response, and is thus important in the prevention and therapy of allergic disorders. The term "antigen desensitization" refers to the process of decreasing an immune response by delivering to a subject, over a period of time, the antigen against which an immune response is mounted. With repeated exposure of the immune cells to the antigen, a decrease in the cytotoxic response is seen. Such desensitization can include, but is not limited to, a switch from a $T_H1$-like response to a $T_H2$-like response to the subject antigen. Antigen desensitization can be used for the treatment of autoimmune and allergic diseases.

An "allergen" is an immunogen which can initiate a state of hypersensitivity, or which can provoke a hypersensitivity reaction in a subject already sensitized with the allergen.

Another aspect of cellular immunity involves an antigen-specific response by helper T lymphocytes ($T_H$ cells). $T_H$ cells act to help stimulate the function, and focus the activity of, nonspecific effector cells against cells displaying peptide antigens in association with MHC molecules on their surface. In addition, various subsets of $T_H$ cells produce distinct cytokines in response to antigenic stimulation. Particularly, antigenic stimulation of naive $T_H$ cells leads to differentiation of the lymphocyte cells into subsets termed "$T_H1$" and "$T_H2$" which have relatively restricted cytokine production profiles and effector functions. $T_H1$ cells secrete IL-2 and IFN-γ, and are the principal effectors of cell-mediated immunity against intracellular microbes and of delayed type hypersensitivity (DTH) reactions. Antibody isotypes stimulated by $T_H1$ cells are effective at activating complement and opsonizing antigens for phagocytosis. $T_H2$ cells produce IL-4 (which stimulates IgE antibody production), IL-5 (eosinophil-activating factor), and IL-10 and IL-13 (which suppress cell-mediated immunity). Thus, the nature of an immune response can be characterized by the profile of antigen-specific lymphocytes that are stimulated by the immunogen, and can be referred to as a "$T_H1$-like" or a "$T_H2$-like" immune response.

The ability of a particular antigen to stimulate a cell-mediated immunological response may be determined by a number of assays, such as by lymphoproliferation (lymphocyte activation) assays, CTL cytotoxic cell assays such as chromium-release assays, or by assaying for T lymphocytes specific for the antigen in a sensitized subject. Such assays are well known in the art (See e.g., Erickson et al., *J. Immunol.*, 151:4189–4199 [1993], and Doe et al., *Eur. J. Immunol.*, 24:2369–2376 [1994]).

As used herein, the term "selectable marker" refers to the use of a gene which encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt) gene which is used in conjunction with hprr cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "compound" refers to any vaccine preparation, chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention of disease.

A compound is said to be "in a form suitable for administration to an animal" when the compound may be administered to an animal by any desired route (e.g., oral, intravenous, subcutaneous, intramuscular, etc.). Administration of a compound to a pregnant female may result in delivery of the compound to the fetuses of the pregnant animal.

As used herein, the term "therapeutic amount" refers to that amount of a compound that is required to neutralize the pathologic effects of an organism, toxin, or other detrimental effects in a subject, or stimulate an appropriate (e.g., effective) immune response in the subject.

A "composition comprising a given polynucleotide sequence" as used herein refers broadly to any composition containing the given polynucleotide sequence. The composition may comprise an aqueous solution.

As used herein, the term "at risk" is used in references to individuals who have been exposed to a pathogenic organism or toxin and may suffer the symptoms associated with infection or disease with the organism or toxin.

The term "sample" as used herein is used in its broadest sense. A "sample suspected of containing a human chromosome or sequences associated with a human chromosome" may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "subject" refers to any animal (i.e., vertebrates and invertebrates), while the term "vertebrate subject" refers to any member of the subphylum Chordata. It is intended that the term encompass any member of this subphylum, including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

DETAILED DESCRIPTION OF THE INVENTION

The AAV vectors and rAAV virions of the present invention can be produced using standard methodology, known to those of skill in the art. The methods generally involve the steps of (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques.

I. AAV Vectors

AAV vectors of the present invention may be constructed using known techniques to provide, as operatively linked components in the direction of transcription, (a) control elements including a transcriptional initiation and termination regions, and (b) a nucleotide sequence encoding an antigen of interest. The control elements are selected to be functional in a targeted recipient cell. The resulting construct which contains the operatively linked components is bounded (5' and 3') with functional AAV ITR sequences.

A. Control Elements

The nucleotide sequences of AAV ITR regions are known (See e.g., Kotin, R. M. (1994) *Human Gene Ther.*, 5:793–801; Bems, K. I. "Parvoviridae and Their Replication" in *Fundamental Virology*, 2nd Edition, (Fields and Knipe, eds.) for the AAV-2 sequence. AAV ITRs used in the vectors of the invention need not have a wild-type nucleotide sequence), and may be altered (e.g., by the insertion, deletion or substitution of nucleotides). Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, (i.e., to allow for excision and replication of the bounded nucleotide sequence of interest when AAV rep gene products are present in the cell).

B. Antigens

Suitable nucleic acid molecules (i.e., nucleic acid encoding at least one antigenic determinant) for use in AAV vectors will generally be less than about 5 kilobases (Kb) in size and will include a first nucleic acid sequence that encodes an antigen or an allergen. If an antigen is used, it will preferably be of an intracellular pathogen, such as a viral, bacterial or parasitic (e.g., protozoan or helminthic) pathogen, or the antigen will be a tumor-specific antigen. However, it is not intended that the present invention be limited to a particular antigen, antigenic determinant, or nucleic acid sequence. It is also not intended that the present invention be limited to any particular size of nucleic acid.

Tumor-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUCI1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) *Mol. Cell. Biol.*, 6:4650–4656) and is deposited with GenBank under Accession No. M14694. Thus, the present invention can be used as immunotherapeutics for cancers including, but not limited to, cervical, breast, colorectal, prostate, lung cancers, and for melanomas.

It is contemplated that suitable viral antigens will be derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and AIDS (e.g., GenBank Accession No. U18552).

It is contemplated that suitable bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemo-*

*philus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

It is also contemplated that antigens useful in the treatment or prevention of autoimmune disorders include, but are not limited to, those derived from nucleosomes for the treatment of systemic lupus erythematosus (e.g., GenBank Accession No. D28394; Bruggen et al., *Ann. Med Interne* (Paris) 147:485–489 [1996]) and from the 44,000 M(r) peptide component of ocular tissue cross-reactive with *O. volvulus* antigen (McKechnie et al., *Ann Trop. Med. Parasitol.*, 87:649–652 [1993]) will also find use in the present invention.

In the treatment or prevention of allergic disorders, the antigen can be an allergen, or an antigen derived from a cell type that will be targeted in a particular therapeutic intervention. For example, interventions targeted against IgE molecules (e.g., to deplete circulating and/or mast cell bound IgE; for example, GenBank Accession No. U39546), can employ antigens derived from an IgE molecule. One particular antigen thus comprises a chimeric molecule containing a portion of an IgE molecule coupled to a foreign carrier protein (Schreiber et al., *Ann. Rev. Immunol.* 6:465 [1988]). Suitable allergens include, but are not limited to, the major and cryptic epitopes of the Der p I allergen (Hoyne et al., *Immunol.*, 83190–195 [1994]), bee venom phospholipase A2 (PLA) (Akdis et al., *J. Clin. Invest.*, 98:1676–1683 [1996]), birch pollen allergen Bet v 1 (Bauer et al., *Clin. Exp. Immunol.*, 107:536–541 [1997]), and the multi-epitopic recombinant grass allergen rKBG8.3 (Cao et al., *Immunol.*, 90:46–51 [1997]).

Polynucleotide sequences coding for the above-described antigens and/or allergens can be obtained using recombinant methods, such as by screening cDNA and genomic libraries from cells expressing the antigen, or by deriving the sequence from a vector known to include the same. Furthermore, the desired sequence can be isolated directly from cells and tissues containing the same, using standard techniques, such as phenol extraction and PCR of cDNA or genomic DNA (See e.g., Sambrook et al., supra, for a description of techniques used to obtain and isolate DNA). Nucleotide sequences encoding an antigen of interest can also be produced synthetically, rather than cloned. The complete sequence can be assembled from overlapping oligonucleotides prepared by standard methods and assembled into a complete coding sequence (See e.g., Edge, *Nature* 292:756 [1981]; Nambair et al., *Science* 223:1299 [1984]; and Jay et al., *J. Biol. Chem.*, 259:6311 [1984]).

C. Tissue-Specific Expression

It is contemplated that in some embodiments, tissue-specific expression will be desireable. Such expression can be achieved by coupling the coding sequence for the antigen of interest with heterologous control elements derived from genes that are specifically transcribed by a selected tissue type. Particularly, the probasin (PB) gene is known to be expressed specifically in the prostatic lobes, and is also detectable in the seminal vesicles (See, Matusik et al., *Biochem. & Cell Biol.*, 64:601 [1986]). A cDNA clone which contains the complete coding region for PB has been described (Spence et al., *Proc. Natl. Acad. Sci. USA* 86:7843 [1989]). Further, the 5' probasin-flanking region has been shown to contain the necessary control sequences for prostatic targeting, and the region will thus direct prostate-specific expression of operably linked coding regions (Greenberg et al., *Endocrine Soc.*, June 9–11: Abstract 1206 [1993]). In the practice of the invention, prostate-specific expression can be effected by coupling the 5'-flanking PB control sequences with the coding region for the antigen of interest. Alternatively, tumor-specific expression can be achieved using control elements obtained from genes that are preferentially transcribed by tumors. Such control elements are termed "tumor-specific" herein. For example, the oncofetal protein carcinoembryonic antigen (CEA) gene is often expressed at high levels in epithelial cancers and gastrointestinal malignancies including colon and pancreatic tumors, but not in normal tissues (Warshaw et al., *N. Engl. J Med.*, 326:455–465 [1992]). Thus, specific gene expression can be readily achieved using the transcriptional regulatory sequence or the promoter of CEA (CEA-P). A number of other suitable genes which are preferentially expressed in tumors have been described, and their promoters and/or other control elements can be included in the present AAV vectors to limit expression in non-tumor cells (Sikora, *Gene Ther.*, 1:149–151 [1994]; Huber et al., *Proc. Natl. Acad. Sci. USA* 88:8039–8043 [1991]; and Austin et al. *Mol. Pharmacol.*, 43:380–387 [1993]).

Examples of other tumor-specific control elements which are useful in the practice of the invention include, but are not limited to, the alpha-fetoprotein (AFP) control sequences (e.g., the promoter and enhancer) to target hepatomas and germ-cell tumors, neuron-specific enolase promoter to target small-cell lung cancer cells, dopa decarboxylase promoter to target neuroectodermal tumors, control sequences for glial fibro acidic protein (GFAP) to target gliomas, prostate-specific antigen (PSA) promoter to target prostate cancer, amylase promoter to target pancreatic cancer, insulin promoter to target pancreatic cancers, thyroglobulin promoter to target thyroid carcinoma, calcitonin promoter to target cancer of the medullary thyroid, promoters for tyrosinase or tyrosinase-related peptide to target melanomas, polymorphic epithelial mucin promoter to target breast cancer, villin promoter to target gastric cancer, gama-glutamyltranspeptidase promoter to target certain hepatic tumors, dopa decarboxylase to target certain lung tumors, c-erbB2 promoter to target breast and gastrointestinal cancer, c-erb3 promoter to target breast cancer, and c-erb4 promoter to target breast and gastric cancer.

A number of tissue-specific promoters have been described above which enable directed expression in selected tissue types. However, control elements used in the present AAV vectors can also comprise control sequences normally associated with the selected nucleic acid sequences. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter, adenovirus major late promoter (Ad MLP), a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available (e.g., from Stratagene).

D. Construction of AAV Vaccine Vectors

The AAV vector which harbors the nucleotide sequence of interest bounded by AAV ITRs (i.e., AAV vaccine vectors), can be constructed by directly inserting selected sequences into an AAV genome with the major AAV open reading frames ("ORFs") excised. Other portions of the AAV genome can also be deleted, so long as a sufficient portion of the ITRs remain to allow for replication and packaging functions. These constructs can be designed using techniques well known in the art (See e.g., U.S. Pat. Nos. 5,173,414 and 5,139,941; International Publication Nos. WO 92/01070 and WO 93/03769; Lebkowski et al., *Mol. Cell. Biol.*, 8:3988–3996 [1988]; Vincent et al., *Vaccines* 90 (Cold Spring Harbor Laboratory Press) [1990]; Carter, *Curr. Opin. Biotechnol.*, 3:533–539 [1992]; Muzyczka, *Curr. Top. Microbiol. Immunol.*, 158:97–129 [1992]; Kotin, *Human Gene Ther.*, 5:793–801 [1994]; Shelling and Smith, *Gene Ther.*, 1:165–169 [1994]; and Zhou et al. *J. Exp. Med.*, 179:1867–1875 [1994]).

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 µg/ml total DNA concentrations (5–100 nM total end concentration). AAV vectors which contain ITRs have been described in (e.g., U.S. Pat. No. 5,139,941, herein incorporated by reference). In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of a selected nucleic acid sequence. The complete chimeric sequence is assembled from overlapping oligonucleotides prepared by standard methods (See e.g., Edge, *Nature* 292:756 [1981]; Nambair et al. *Science* 223:1299 [1984]; and Jay et al. *J. Biol. Chem.*, 259:6311 [1984]).

II. rAAV Virions

In order to produce rAAV virions for use as immunogens or antigens (i.e., AAV vaccine preparations), an AAV vector constructed as described above is introduced into a suitable host cell using known techniques (e.g., transfection). A number of transfection techniques are generally known in the art (See e.g., Graham et al., *Virol.*, 52:456 [1973], Sambrook et al. supra, Davis et al., supra, and Chu et al., *Gene* 13:197 [1981]). Particularly suitable transfection methods include calcium phosphate co-precipitation (Graham et al., *Virol.*, 52:456–467 [1973]), direct microinjection into cultured cells (Capecchi, *Cell* 22:479–488 [1980]), electroporation (Shigekawa et al., *BioTechn.*, 6:742–751 [1988]), liposome-mediated gene transfer (Mannino et al., *BioTechn.*, 6:682–690 [1988]), lipid-mediated transduction (Felgner et al., *Proc. Natl. Acad. Sci. USA* 84:7413–7417 [1987]), and nucleic acid delivery using high-velocity microprojectiles (Klein et al., *Nature* 327:70–73 [1987]).

For the purposes of the invention, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, as indicated above, a "host cell" as used herein generally refers to a cell which has been transfected with an exogenous DNA sequence. Cells from the stable human cell line, 293 (ATCC Accession No. CRL1573) are preferred in the practice of the present invention. Particularly, the human cell line 293 is a human embryonic kidney cell line that has been transformed with adenovirus type-5 DNA fragments (Graham et al., *J. Gen. Virol.*, 36:59 [1977]), and expresses the adenoviral E1a and E1b genes (Aiello et al., *Virol.*, 94:460 [1979]). The 293 cell line is readily transfected, and provides a particularly convenient platform in which to produce rAAV virions.

Host cells containing the above-described AAV vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV ORFs, namely the rep and cap coding regions, or functional homologues thereof.

AAV helper functions are introduced into the host cell by transfecting the host cell with an AAV helper construct either prior to, or concurrently with, the transfection of the AAV vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products (See e.g., Samulski et al., *J. Virol,.* 63:3822–3828 [1989]; and McCarty et al.,*J. Virol.*, 65:2936–2945 [1991]). A number of other vectors have been described which encode Rep and/or Cap expression products (See e.g., U.S. Pat. No. 5,139,941, herein incorporated by reference).

Both AAV vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the gene encoding aminoglycoside phosphotranferase (APH) that allows selection in mammalian cells by conferring resistance to G418 (Sigma). Other suitable markers are known to those of skill in the art.

The host cell (or packaging cell) must also be rendered capable of providing nonAAV derived functions, or "accessory functions," in order to produce rAAV virions. Accessory functions are nonAAV derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of rep and cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents (See e.g., Buller et al., *J. Virol.*, 40:241–247 [1981]; McPherson et al., *Virol.*, 147:217–222 [1985]; and Schlehofer et al., *Virol.*, 152:110–117 [1986]).

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, virus, transposon or cosmid. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of adenovirus, or constructed using recombinant or synthetic methods known in the art. In this regard, adenovirus-derived accessory functions have been widely studied, and a number of adenovirus genes involved in accessory functions have been identified and partially characterized (See e.g., Carter, "Adeno-Associated Virus Helper Functions," in *CRC Handbook of Parvoviruses*, Vol. I (P. Tijssen, ed.) [1990], and Muzyczka, *Curr. Top. Microbiol. Immun.*, 158:97–129 [1992]). Specifically, early adenoviral gene regions E1a, E2a, E4, VAI RNA and, possibly, E1b are thought to participate in the accessory process (Janik et al., *Proc. Natl. Acad. Sci. USA* 78:1925–1929 [1981]). Herpesvirus-derived accessory functions have been described (See e.g., Young et al., *Prog. Med. Virol.*, 25:113 [1979]). Vaccinia virus-derived accessory functions have also been described (See e.g., Carter, supra., and Schlehofer et al., *Virol.*, 152:110–117 [1986]).

As a consequence of the infection of the host cell with a helper virus, or transfection of the host cell with an accessory function vector, accessory functions are expressed which transactivate the AAV helper construct to produce AAV Rep and/or Cap proteins. The Rep expression products direct excision of the recombinant DNA (including the DNA of interest) from the AAV vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if helper virus infection is employed to express the accessory functions, residual helper virus can be inactivated, using known methods. For example, adenovirus can be inactivated by heating to temperatures of approximately 60° C. for approximately 20 minutes or more, as appropriate. This treatment selectively inactivates the helper adenovirus which is heat labile, while preserving the rAAV which is heat stable.

III. Pharmaceutical Compositions

The resulting rAAV virions are then ready for use in pharmaceutical compositions which can be delivered to a subject to immunize against the selected antigen or antigens, to desensitize the subject against the selected antigen or allergen, or to elicit a shift in the profile of an immune response (e.g., a switch from a $T_H1$-like response to a $T_H2$-like response). Pharmaceutical compositions comprise sufficient genetic material to produce a therapeutically effective amount of the antigen to elicit an immune response. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in *Remington's Pharmaceutical Sciences* (Mack Pub. Co., N.J. [1991]).

Vaccine compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Vaccine preparations for oral use can be provided by preparing combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations which can be used orally include push-fit capsules made of gelatin, as well as soft, sealed capsules made of gelatin and a coating, such as glycerol or sorbitol. Push-fit capsules may contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of AAV vaccine preparations, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

Appropriate doses will depend, among other factors, on the mammal being immunized (e.g., human or nonhuman primate or other mammal), age and general condition of the subject, the severity of the disease or cancer being treated or prevented, and the selected antigen employed and the mode of administration. In addition, the goal of the immunization will dictate the amount, concentration and frequency of the dose, for example wherein desensitization and/or a shift in the type of immune response is desired. An appropriate effective amount can be readily determined by one of skill in the art.

Thus, a "therapeutically effective amount" will fall in a relatively broad range that can be determined through clinical trials. For example, in the case of in vivo transductions (i.e., injection directly into tissue), a therapeutically effective dose will be on the order of from about $10^3$ to $10^{15}$ of the rAAV virions. Other effective dosages can be readily established by one of ordinary skill in the art through routine trials establishing dose response curves.

It is intended that the dosage treatment and regimen used with the present invention will vary, depending upon the subject and vaccine preparation to be used. Thus, the dosage treatment may be a single dose schedule or a multiple dose schedule. Moreover, the subject may be administered as many doses as appropriate. One of skill in the art can readily determine an appropriate number of doses based on criteria including, but not limited to, the patient's age, immune status, the antigen(s) used in the vaccine, etc. A multiple dose schedule is one in which a primary course of vaccination may be with 1–10 separate doses, followed by other doses given at subsequent time intervals, chosen to maintain and/or reinforce the immune response. In one aspect of the invention, vaccination is achieved using a single dose. The dosage regimen will also, at least in part, be dependent on the judgment of the ordinarily skilled practitioner. If prevention of disease is desired, the vaccines are generally administered prior to primary infection with the pathogen of interest or prior to onset of the cancerous condition. If treatment is desired (e.g., the reduction of symptoms or recurrences), the vaccines are generally administered subsequent to primary infection or onset of the cancerous condition.

Direct delivery of the pharmaceutical compositions in vivo will generally be accomplished via injection using a conventional syringe. In this regard, the compositions can be injected either subcutaneously, epidermaly, intradermally, intrathecally, intraorbitally, intramucosally (e.g., nasally, rectally and vaginally), intraperitoneally, intravenously, orally, or intramuscularly. Other modes of administration include oral and pulmonary administration, suppositories, and transdermal applications.

One skilled in the art will recognize that the methods and compostions described above are also applicable to a range of other treatment regimens known in the art. For example, the methods and compositions of the present invention are compatible with ex vivo therapy (e.g., where cells are removed from the body, incubated with the recombinant AAV vector, and the treated cells are returned to the body).

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

In the experimental disclosure which follows, the following abbreviations apply: N (Normal); M (Molar); mM (millimolar); $\mu$M (micromolar); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); $^{51}$Cr (Chromium 51); $\mu$Ci (microcurie); ° C. (degrees Centigrade); pH (hydrogen ion concentration); NaCl (sodium chloride); HCl (hydrochloric acid); OD (optical density); bp (base pair(s)); ATP (adenosine 5'-triphosphate); PCR (polymerase chain reaction); DNA (deoxyribonucleic acid); cDNA (complementary DNA); AAV (adeno-associated virus); rAAV (recombinant adeno-associated virus); CMV (cytomegalovirus); MHC (major histocompatibility complex); ITR (inverted terminal repeat); β-gal (β-galactosidase); FCS (fetal calf serum); CFA (complete Freund's adjuvant); BSA (bovine albumin); ER (endoplasmic reticulum); ATCC (American Type Culture Collection, Rockville, Md.); Sigma (Sigma Aldrich, St. Louis, Mo.); Zymed (Zymed Laboratories, South San Francisco, Calif.); Gemini (Gemini Bioproducts, Calabasas, Calif.); BioWhittaker (BioWhittaker, Walkersville, MC); DuPont (DuPont, Wilmington, Del.); and Stratagene (Stratagene Cloning Systems, La Jolla, Calif.).

Vector Constructs, Encapsidation and Cell Lines:

The AAV-Ova vector was constructed by placing the 1.8 kb HindIII-BamHI Ova cDNA fragment from the pBSOva19 plasmid (provided by K. Rock, see, Rock, *Immunol. Today* 17: 131 [1995]) into the HindIII-BglII site of the multiple cloning sequence of pV4.1cmod. The pV4.1cmod plasmid was constructed as follows. pV4.1c is an expression vector that contains the CMV immediate-early promoter, a chimeric CMV-beta-globin intron, a polylinker, and the human growth hormone polyadenylation sequence. The pV4.1c plasmid was constructed using a synthetic DNA encoding the restriction sites NotI-MluI-Ecl136II-SstI-SfuI-SmaI-SfuI-ClaI-BglII-SnaBI-BstEII-PmlI-RsrII-NotI, and having the following nucleotide sequence:

5'-GCGGCCGCACGCGTGAGCTCCGCGGTTCGAAT CCCGGGATTCGAACATC GATAAAAGATCTACG-TAGGTAACCACGTGCGG

ACCGAGCGGCCGC- 3' (SEQ ID NO.: 1), that was cloned into the blunted KasI and EarI(partial) sites of pUC119 to provide a 2757 bp intermediate plasmid. A 653 bp SpeI(blunted)-SacII(blunted) fragment encoding the CMV immediate early (CMV-IE) promoter, and a 488 bp SmaI-DraIII fragment containing the human growth hormone polyadenylation site, were cloned into the Ecl136II and SnaBI sites of the intermediate plasmid. A chimeric intron having the splice donor from the first intron of the CMV-IE gene, and the splice acceptor from the second intron of the human β-globin gene, was then inserted into the SmaI site of the plasmid in two steps. First, a DNA fragment encoding the CMV-IE gene first intron splice donor was produced by PCR using isolated CMV DNA (strain ad169) as template, and the following primers: 5'-GGCCGGGAACGGTGCATT-3' (SEQ ID NO.: 2) and 5'-GGGCAAGGGGGTGGGCCTATA-3' (SEQ ID NO.: 3). The resulting 87 bp fragment was ligated into the SmaI site of the intermediate plasmid. The resulting construct was cleaved with BstXI and SmaI, blunted with T4 DNA polymerase, and a 398 bp DraI-EcoRI(blunt) fragment encoding the human β-globin second intron splice acceptor was ligated into the construct. The pV4.1c plasmid was completed by ligation of a synthetic polylinker encoding the restriction sites: ClaI-EcoRI-SmaI-BamHI-XbaI-SalI-PstI-HinDIII-XhoI-Eco47III-XhoI-BglII, having the following nucleotide sequence:

5'-ATCGATTGAATTCCCCGGGGATCCTCTAGAGTC GACCTGCAGAAGCTTGC TCTCGAGCAGCGCTGCTCGAGAGATCT-3' (SEQ ID NO.: 4), between the ClaI and BglII sites of the intermediate plasmid.

Then, pUC119 was digested with AflIII and EheI, dephosphorylated, and the resulting 2591 bp fragment containing the coli 1 origin and the amp gene was isolated. This vector was ligated to synthetic DNA encoding a single Sse8387 I site which is comprised of the phosphorylated oligonucleotides PVMOD1 (5'-GCCCCTGCAGGA-3', SEQ ID NO.: 5) and PVMOD2 (5'-CATGTCCTGCAGGGGC-3', SEQ ID NO.: 6). The resulting plasmid was digested with Sse8387 I and dephosphorylated. Plasmid pV4.1c was digested with Sse8387 I, and the 1767 bp ITR-bounded, CMV-driven expression cassette was isolated and ligated to the above-described vector to provide the pV4.1 cmod construct. This construct thus contains the CMV promoter, followed by the CMV splice donor, the human β-globin splice acceptor, the multiple cloning site and the human growth hormone polyadenylation signal, flanked by AAV ITRs. A 624-bp blunt-ended HpaI noncoding sequence was then cloned into the PmlI site as a spacer fragment (FIG. 1A). FIGS. 1A and 1B provide a schematic illustration of the construction of the recombinant AAV virions rAAV-Ova (containing the cDNA encoding ovalbumin) and rAAV-LacZ (containing the cDNA encoding β-galactosidase from *E. coli*). In these Figures, "ITR" indicates inverted terminal repeats; "CMV" indicates the CMV promoter; "An" indicates human growth hormone polyadenylation signal; and "∅" indicates a noncoding 624 bp fragment from the lacZ gene.

The AAV-lacZ vector contains the *Escherichia coli* β-galactosidase (β-gal) gene under the transcriptional control of the CMV immediate early promoter (FIG. 1B) as previously described (See e.g., Kessler et al. (1996) *Proc. Natl. Acad. Sci. USA* 24:14082–14087). The human 293 cell line was cultured in complete DMEM (BioWhittaker) containing 4.5 g/liter glucose, 10% heat-inactivated fetal calf serum (FCS, Gemini), 2 mM glutamine, 50 units/ml penicillin, and 50 µg/ml streptomycin. The cell lines, M05 20.10 (B16 melanoma, stably transfected with the ovalbumin gene; provided by K. Rock (See, Falo et al., Nature Medicine 1: 649 [1995]), B3Z, RMA-S, EL-4 and the ovalbumin-transfected cell line EG.7 Ova (obtained from ATCC), were cultured in RPMI (BioWhittaker) containing 10% heat-inactivated FCS, 2 mM glutamine, 50 units/ml penicillin, 50 µg/ml streptomycin, and 50 mM pyruvate.

The rAAV virions were produced in the 293 cells as previously described. Kessler et al. (1996) *Proc. Natl. Acad. Sci. USA* 24:14082–14087, Colosi et al. (1995) *Blood* 86 no. Suppl 1:627a (Abstr.). Subconfluent 293 cells were co-transfected by calcium phosphate precipitation with either the AAV-Ova or AAV-LacZ expression vectors flanked by ITRs, an adenoviral helper vector, and a helper vector supplying AAV Rep and Cap functions. After 72 hours of culture, pelleted cells were lysed in Tris buffer (10 mM Tris/150 mM NaCl, pH 8.0) by three cycles of freeze-thaw. The lysate was clarified of cell debris by centrifugation at 12,000×g, followed by cesium chloride isopyknic gradient centrifugation. rAAV virions were extracted from the resulting gradient by isolating the fractions with an average density of 1.38 g/ml, followed by resuspension in Hepes buffered saline containing 50 mM Hepes (pH 7.4) and 150 mM NaCl. Viral titer was determined by quantitative dot-blot-hybridization of DNase-treated stocks and was routinely in the range of $10^{12}$–$10^{13}$ particles/ml, with the particle-to-transduction unit (AAV-lacZ) ratio between $10^2$ and $10^3$.

EXAMPLE 1

Immunogenicity of rAAV Virions

The following studies were carried out to assess the immunogenicity of rAAV virions. rAAV-Ova virions (FIG. 1A) containing the ovalbumin gene under the control of the cytomegalovirus (CMV) promoter were constructed (as described above) and a single dose of $3\times10^{11}$ viral particles was administered by different routes to groups of C57BL/6 mice. Another rAAV virion, rAAV-lacZ (FIG. 1B), served as a control.

A. Immunization of Mice: 6- to 8-week old female C57BL/6 mice were used in these studies. Prior to intramuscular (IM) administration of rAAV, the mice received methoxyflurane anesthesia. The mice received $3\times10^{11}$ rAAV particles by injecting 50 μl of Dulbecco's phosphate buffered saline (DPBS) containing 1.5×10¹¹ rAAV particles into the quadriceps muscle of each leg using a 27 gauge needle and a syringe. Other groups of mice were injected with 3×10¹¹ rAAV either subcutaneously (SC) at the base of the tail, intravenously (IV) into the lateral tail vein, or intraperitoneally (IP). Control mice received 100 μl of a mixture containing equal volumes of ovalbumin (2 mg/ml) in DPBS and complete Freund's adjuvant (CFA) intraperitoneally.

B. ELISA: To analyze the humoral response induced by rAAV-Ova, the sera of treated mice were obtained 14 or 28 days after administration of rAAV-Ova and analyzed by ELISA for the presence of antibodies to ovalbumin (FIG. 2A) or AAV-derived proteins (FIG. 2B).

Immulon plates (96-well) were coated overnight at 4° C. with 50 μl of either 15 μg/ml ovalbumin (Grade VI, Sigma) or 1×10¹⁰ rAAV-LacZ virions in 0.1 M carbonate-bicarbonate buffer, pH 9.5. The plates were washed with 50 mM TRIS buffered saline, pH 8.0, 0.05% Teen 20 (TTBS, Sigma) and blocked with 3% BSA in TTBS for 3 hours at room temperature. Mouse sera were diluted with TTBS, added to the plates and incubated at room temperature for 1 hour, after which a 1:5000 dilution of horseradish peroxidase-conjugated rabbit anti-mouse IgG (Zymed) was added. The plates were washed and developed with the substrate TMB (Zymed). The reaction was stopped with 1 N HCl and the OD was read at 450 nm on microplate reader (DuPont).

Figure 2:
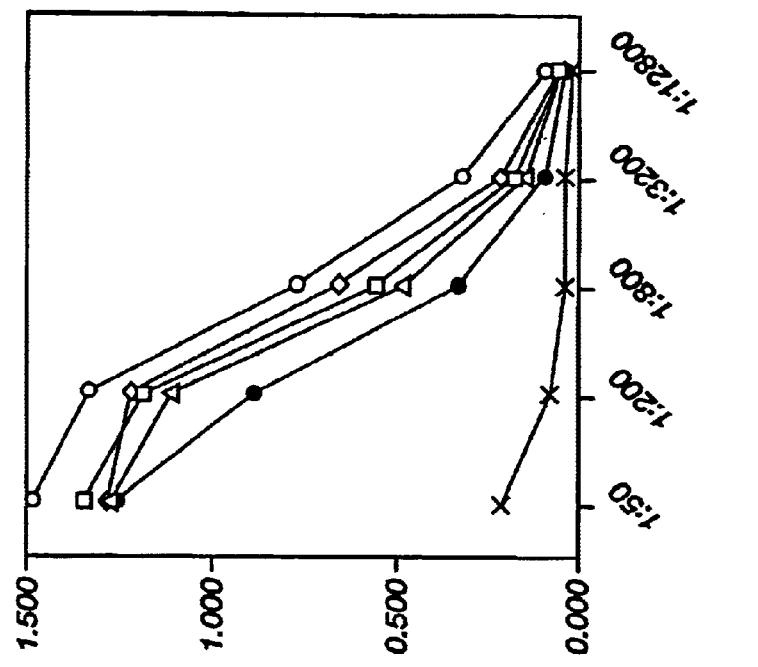
Figure 2:
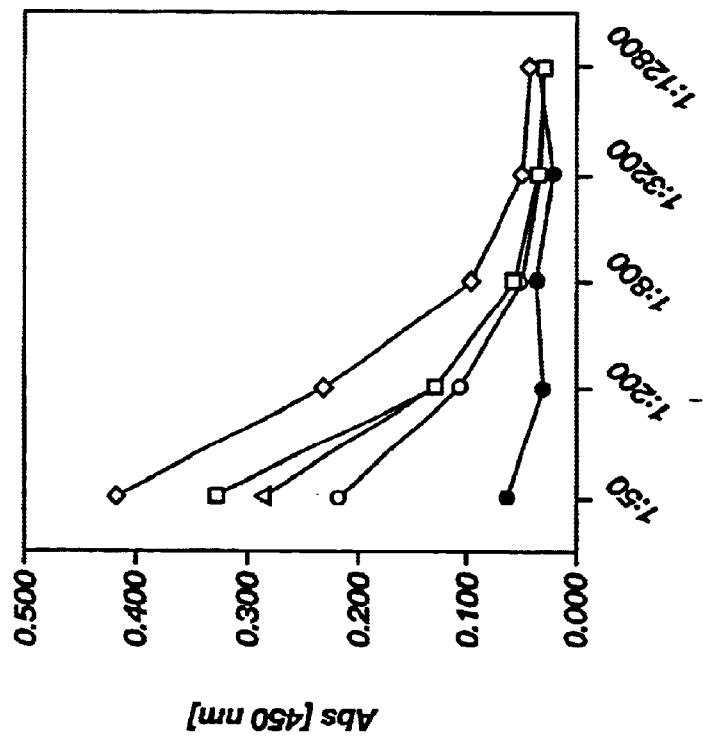

The ELISA results are depicted in FIGS. 2A and 2B. In these Figures, the results for C57BL/6 mice injected with 3×10¹¹ rAAV-Ova virions intramuscularly (open squares), subcutaneously (open diamonds), intraperitoneally (open circles) or intravenously (open triangles) are indicated. The control groups received either 3×10¹¹ rAAV-lacZ virions subcutaneously (solid diamonds) or 100 μl of Ova/CFA intraperitoneally (crosses). Day 28 sera were analyzed for the presence of antibodies using either ovalbumin- (FIG. 2A) or rAAV-LacZ-coated (FIG. 2B) ELISA plates. The results represent the means of sera from 3 mice per group. Although none of the rAAV-Ova treated groups had detectable anti-ovalbumin antibodies at day 14, by day 28 such antibodies were clearly demonstrated, regardless of the route of virus administration (FIG. 2A). Interestingly, all of the mice which received rAAV virions developed a humoral response to viral proteins, by day 14 (FIG. 2B).

C. Assay for CTL: To assess the ability of rAAV-Ova to elicit a CTL response, recipient spleen (and in the case of SC administration, draining lymph node) cells were harvested 14 days after administration of the rAAV virions and restimulated, in vitro, with EG.7 Ova cells. More particularly, single cell suspensions from three mice per group were pooled and the lymphocytes were separated by density gradient centrifugation using Lympholyte-M (Accurate Chemical). To expand CTLs, 5×10⁶ cells/ml were cultured with 5×10⁵ irradiated (6000 rad) EG.7 Ova cells for 7 days in 24 well-plates, containing RPMI medium supplemented with 10% FCS, 50 units/ml penicillin, 50 μg/ml streptomycin, sodium pyruvate, MEM non-essential amino acids, 50 μM 2-ME, and 5 units/ml rhIL-2.

CTL activity was determined in a ⁵¹Cr-release assay. In particular, on day 7, EL-4 cells of EG.7 Ova cells were labeled with 100 μCi ⁵¹Cr for 1 hour at 37° C. and used as target cells with E:T ratios of between 100:1 and 12:1. After 4 hours at 37° C., supernatants were harvested with Optiphase scintillation fluid (Wallac Oy) and counted in a Microbeta scintillation counter (Wallac). Percent specific lysis was determined by the formula:

100× experimental release-spontaneous release maximum release-spontaneous release Maximum release was determined by lysis of the target cells in PBS containing 0.5% Triton-X-100. Spontaneous release was always less than 10% maximum release.

Figure 3:
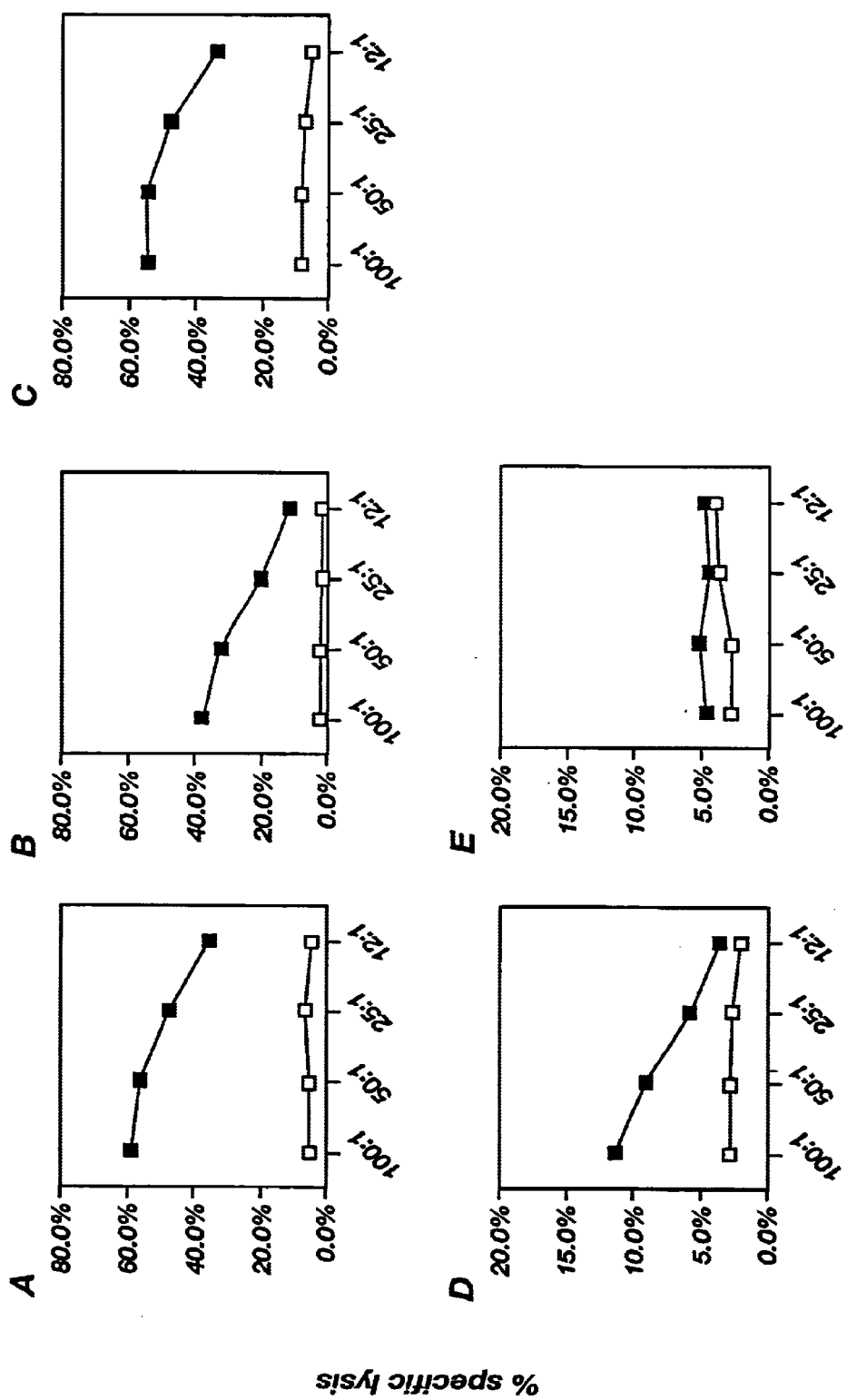

FIG. 3 shows that lymphocyte preparations from recipients of rAAV-Ova, but not rAAV-lacZ, contained CTL that lyse EG.7 Ova cells in a dose dependent manner. EL-4 cells, which do not express ovalbumin, but are otherwise identical to EG.7 Ova cells, were not lysed by these CTLs. The results for cytolytic activity against ⁵¹Cr-labeled EL-4 (open squares) or EG.7 Ova (solid squares) are indicated in this Figure. The results for various routes of administration are shown in this Figure, with the results for rAAV particles administered subcutaneously shown in FIG. 3, Panels A and E, the results for intraperitoneally administered rAAV particles shown in FIG. 3, Panel B, the results for intravenously administered rAAV particles shown in FIG. 3, Panel C, and the results for intramuscularly administered rAAV particles shown in FIG. 3, Panel D. The data shown are from single experiment which is representative of three experiments conducted with similar results.

As the results indicate, although all routes of administration led to the induction of ovalbumin-specific CTL, the intramuscular (IM) route was the least efficient. In other studies, ovalbumin-specific CTLs were also obtained from mice 6 weeks after a single administration of rAAV-Ova, although again the IM route was the least efficient.

EXAMPLE 2

In Vivo Protection Study

To determine if rAAV virions can be used to elicit protective anti-tumor immunity, a tumor model based on the ovalbumin-transfected murine melanoma cell line B16 (MO5 20.10) was used, which expresses a H-2K$^b$- restricted ovalbumin specific CTL epitope (Falo et al. (1995) *Nat. Med.*, 1:649–653; Condon (1996) *Nat. Med.*, 2:1122–1128).

C57BL/6 (n=5) mice were injected once with either 3×10¹¹ rAAV-Ova virions, 3×10¹¹ rAAV-lacZ virions, or DPBS intraperitoneally on day 0. After 14 days, mice were challenged subcutaneously with 1×10⁵ MO5 20.10 cells in the left flank, after which they were monitored daily for the appearance of tumors at the injection site. Tumors>3 mm in diameter were scored positive. Mice with tumors>2 cm in diameter were sacrificed.

TABLE I

Development of Protective Anti-Tumor Immunity Following a Single Injection of AAV-Ova in C57BL/6 mice

| Immunization* | No. of Tumor-Bearing Mice |
|---|---|
| DPBS | 5/5 |
| AAV-lacZ | 4/5 |
| AAV-Ova | 1/5 |

*C57BL/6 mice were injected intraperitoneally with 3 × 10¹¹ rAAV particles and 14 days later challenged subcutaneously with 1 × 10⁵ MO5 20.10 cells in the left flank. After tumor challenge, mice were monitored daily. Tumors > 3 mm in diameter were scored positive. Mice with tumors > 2 cm in diameter were sacrificed.

As shown in Table 1, 100% (5 of 5) mice injected with phosphate buffered saline (DPBS) and 4 of 5 mice injected with rAAV-lacZ developed easily visible tumors within 12 days of tumor challenge. By contrast, only one 1 of 5 mice injected with rAAV-Ova developed a tumor, which delayed in appearance by comparison to the other experimental groups.

EXAMPLE 3

Ability of rAAV-Ova to Deliver Transgene Product into the MHC Class I Pathway Peptides presented in the context of MHC Class I are usually derived from proteins which are expressed endogenously in the cell. Virus-encoded proteins expressed by the cell are typically processed in the cytosol, transported into the ER and presented on the cell surface in association with MHC Class I determinants (Monaco, J. (1992) *Immunol. Today* 13:173–178; Rock, K. (1995) *Immunol. Today* 17:131–137). To investigate if rAAV-Ova delivers the transgene product into the class I pathway, irradiated EL-4 cells were co-cultured for 18–24 hours with various doses of rAAV virions (rAAV-Ova or rAAV-lacZ), after which they were tested for the ability to stimulate IL-2 secretion of an MHC class I restricted CD8$^+$ T cell hybridoma B3Z (Karttunen et al. (1992) *Proc. Natl. Acad. Sci. USA* 89:6020–6024), specific for residues 257–264 of ovalbumin.

CTL Proliferation Assay: Stimulation of the CD8$^+$ T cell hybridoma (B3Z,H-2K$^b$) was measured by incubating the hybridoma (5×10$^5$) with variable numbers of histocompatible EL-4 cells (C57BL/6, H-2K$^b$, thymoma), which had been contacted for 18 to 24 hours with rAAV-Ova or rAAV-lacZ virions. IL-2 concentration in supernatants (50 μl) taken after 24 hours was measured as previously described using the IL-2 dependent cell line, HT-2 (Kim et al., *J. Immunol.*, 156:2737–2742 [1996]) which had been pulsed with 1 μCi of [$^3$H]-thymidine for 4 hours. Incorporation of [$^3$H]-thymidine was determined in a Microbeta scintillation counter (Wallac).

Figure 4:
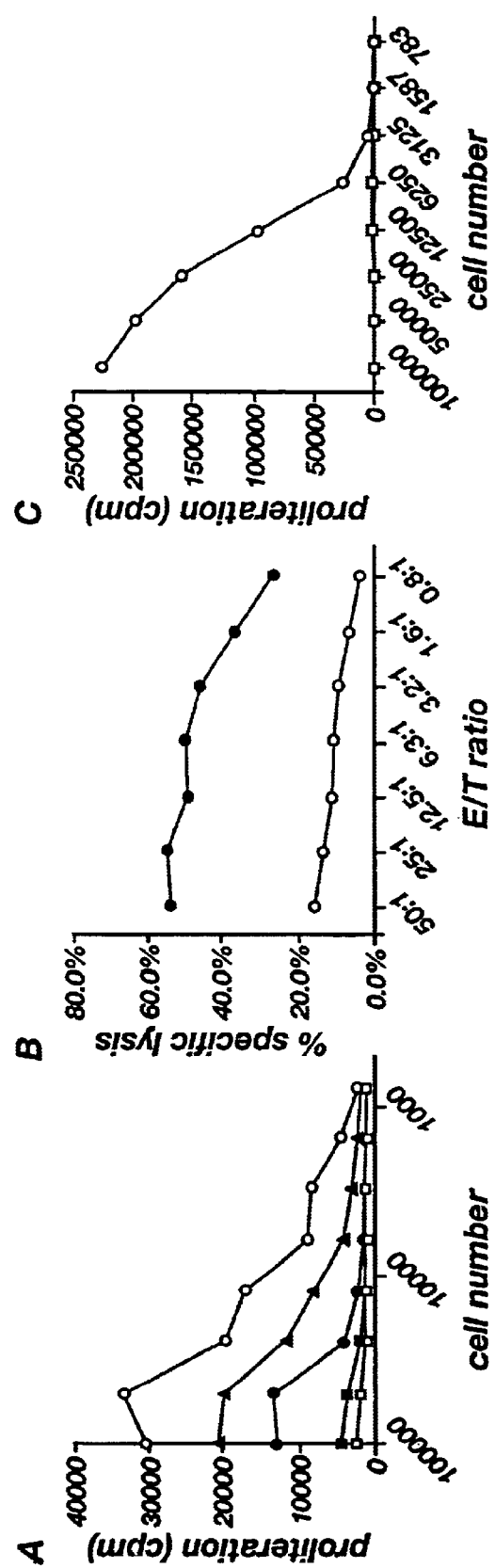

The results from these experiments are shown in FIG. 4. FIG. 4A shows the results for the H-2K$^b$T cell line, EL-4 (irradiated at 3000 rad) incubated overnight with either: 10$^9$ (solid squares), 10$^{10}$ (solid circles) or 10$^{11}$ (solid triangles) rAAV-Ova virions; the immunodominant K$^b$-restricted ovalbumin peptide SINFEKL (SEQ ID NO.: 7) (residues 257–264) (open circles); or 1×10$^{11}$ rAAV-lacZ virions (open squares). These cells were washed and various numbers incubated with 50,000 cells of the CD8$^+$ ovalbumin-specific T cell hybridoma, B3Z, for 24 hours and the amount of IL-2 secreted was determined by [3H]-thymidine incorporation by HT-2 cells.

FIG. 4B shows the results of experiments in which a MHC class I-restricted, ovalbumin-specific CTL line was used to evaluate the susceptibility to lysis of rAAV-transduced target cells in a $^{51}$Cr release assay. In this Figure, the results are shown for irradiated EL-4 cells transduced either with rAAV-Ova (solid circles) or rAAV-lacZ (open circles) overnight and used as target cells. In FIG. 4C, results are shown for the TAP-2 deficient cell line RMA-S (irradiated at 3000 rad) incubated overnight with either: 10$^{11}$ rAAV-Ova virions (solid triangles); the immunodominant K$^b$ restricted ovalbumin peptide SINFEKL (SEQ ID NO.: 7) (residues 257–264) (open circles); or 1×1011 rAAV-lacZ virions (open squares). The secreted IL-2 was determined as previously described.

As seen in FIG. 4A, EL-4 cells receiving rAAV-Ova, but not rAAV-lacZ, stimulated the ovalbumin-specific T cell hybridoma in a dose dependent manner. Further, use of a higher number of transducing particles led to an increased stimulation of the T cell hybridoma. EL-4 cells transduced with rAAV-Ova were also susceptible to lysis by an ovalbumin-specific, Class I MHC restricted CTL line (FIG. 4B). The level of killing of these targets was comparable to that of EG.7 Ova cells, which are stably transfected with the ovalbumin gene.

To confirm that cytosolic degradation of the transgene product is required for loading of MHC class I molecules in rAAV infected cells, TAP-2 deficient RMA-S cells (Attaya et al. (1992) *Nature* 355:647–649) were infected with rAAV-Ova for 18 hours and the ability of these cells to present ova-derived peptides was analyzed in the hybridoma assay (FIG. 4C). Although expression of ovalbumin in the transduced RMA-S cells was confirmed by immunoblot, no stimulation of the B3Z cell line could be detected, presumably due to the inability of the cell line to transport peptides from the cytosol into the ER. By contrast, peptide-pulsed RMA-S cells were perfectly capable of stimulating the ova-specific hybridoma (FIG. 4C).

Thus, the present invention clearly provides novel methods for eliciting an immune response in a vertebrate subject using AAV vectors, as well as methods of making and using AAV vectors, and recombinant AAV virions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, vaccine design, or related fields are intended to be within the scope of the following claims.

SEQUENCE LISTING

<160> NUMBER OF SEQ ID NOS: 7

<210> SEQ ID NO 1
<211> LENGTH: 94
<212> TYPE: DNA
<213> ORGANISM: Artificial Sequence
<220> FEATURE:
<223> OTHER INFORMATION: Description of Artificial Sequence: Synthetic

<400> SEQUENCE: 1

```
gcggccgcac gcgtgagctc cgcggttcga atcccgggat tcgaacatcg ataaaagatc      60
tacgtaggta accacgtgcg gaccgagcgg ccgc                                  94
```

-continued

```
<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 2
ggccgggaac ggtgcatt                                                 18

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 3
gggcaagggg gtgggcctat a                                             21

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic

<400> SEQUENCE: 4
atcgattgaa ttccccgggg atcctctaga gtcgacctgc agaagcttgc tctcgagcag   60
cgctgctcga gagatct                                                  77

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 5
gcccctgcag ga                                                       12

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 6
catgtcctgc aggggc                                                   16

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Ova
      peptide Ser Ile Ile Asn Phe Glu Lys Leu
1               5
```

We claim:

1. A method of eliciting an immune response in a mammalian subject comprising:

providing a recombinant AAV virion containing a nucleic acid molecule encoding at least one tumor-specific antigen operably linked to control sequences which direct the expression of said tumor-specific antigen in a suitable recipient cell; and introducing said recombinant AAV virion into a recipient cell of said mammalian subject under conditions that permit the expression of said tumor-specific antigen, wherein the expression of said tumor-specific antigen elicits an immune response to said tumor-specific antigen.

2. The method as claimed in claim 1, wherein the nucleic acid molecule encodes a melanoma-associated antigen.

3. The method as claimed in claim 1, wherein the nucleic acid molecule encodes melanoma-associated antigen E1.

4. The method as claimed in claim 1, wherein the nucleic acid molecule encodes melanoma-associated antigen E3.

5. The method as claimed in claim 1, wherein the nucleic acid molecule encodes melanoma-associated antigen E3.

6. The method as claimed in claim 1, wherein the nucleic acid molecule encodes melanoma-associated antigen E4.

7. The method as claimed in claim 1, wherein the nucleic acid molecule encodes a tyrosinase.

8. The method as claimed in claim 1, wherein the nucleic acid molecule encodes mutate ras.

9. The method as claimed in claim 1, wherein the nucleic acid molecule encodes mutant p53.

10. The method as claimed in claim 1, wherein the nucleic acid molecule encodes p97 melanoma antigen.

11. The method as claimed in claim 1, wherein the nucleic acid molecule encodes p53 peptide associated with advance cancers.

12. The method as claimed in claim 1, wherein the nucleic acid molecule encodes a human papillomavirus antigen.

13. The method as claimed in claim 12, wherein the nucleic acid molecule encodes the E6 antigen.

14. The method as claimed in claim 12, wherein the nucleic acid molecule encodes the B7 antigen.

15. The method as claimed in claim 1, wherein the nucleic acid molecule encodes MUC1-KLH.

16. The method as claimed in claim 1, wherein the nucleic acid molecule encodes carcinoembryonic antigen.

17. The method as claimed in claim 1, wherein the nucleic acid molecule encodes MART1 antigen.

18. The method as claimed in claim 1, wherein the nucleic acid molecule encodes a PSA antigen.

* * * * *